United States Patent
Tachikawa

(10) Patent No.: US 9,888,900 B2
(45) Date of Patent: Feb. 13, 2018

(54) IMAGING MANAGEMENT APPARATUS, X-RAY IMAGING SYSTEM, METHOD FOR PROCESSING INFORMATION, AND PROGRAM

(71) Applicant: CANON KABUSHIKI KAISHA, Tokyo (JP)

(72) Inventor: Hirohide Tachikawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 147 days.

(21) Appl. No.: 14/875,429

(22) Filed: Oct. 5, 2015

(65) Prior Publication Data

US 2016/0095567 A1 Apr. 7, 2016

(30) Foreign Application Priority Data

Oct. 7, 2014 (JP) ................................. 2014-206744

(51) Int. Cl.
  *A61B 6/00* (2006.01)
(52) U.S. Cl.
  CPC .............. *A61B 6/542* (2013.01); *A61B 6/465* (2013.01); *A61B 6/563* (2013.01)

(58) Field of Classification Search
  CPC ................................ A61B 6/542; A61B 6/563
  See application file for complete search history.

(56) References Cited

U.S. PATENT DOCUMENTS 9,538,977 B2 * 1/2017 Sato ....................... A61B 6/542

FOREIGN PATENT DOCUMENTS

JP 2006-340910 A 12/2006

* cited by examiner

*Primary Examiner* — Dani Fox
(74) *Attorney, Agent, or Firm* — Canon USA Inc., IP Division

(57) ABSTRACT

A dose measured from region information, X-ray information, and a captured image in a previous imaging operation and a dose of radiation obtained from a DAP meter are saved as pieces of information. A dose used in a first imaging operation is based on the saved pieces of information, and a dose to be used in a second imaging operation is estimated from region information or X-ray information in the second imaging operation. If there is a significant difference between the dose in the first imaging operation and the estimated dose for the second imaging operation, a warning is issued. If an image of a region is captured for testing purposes, a warning is not issued.

17 Claims, 13 Drawing Sheets

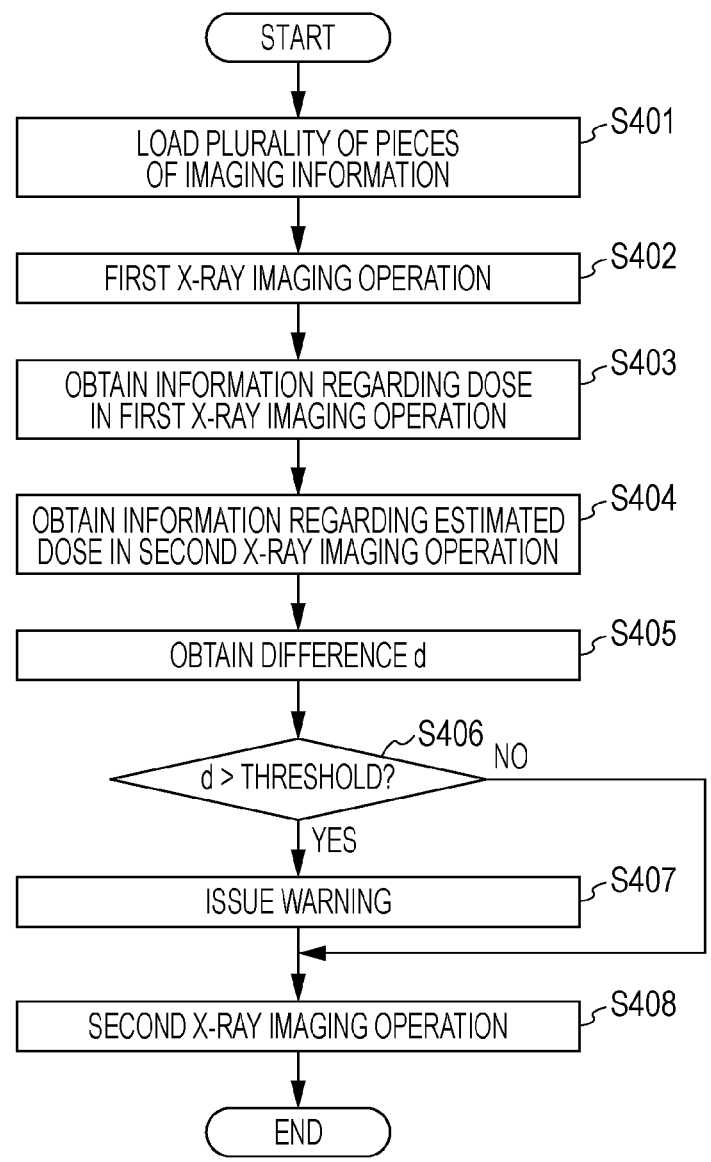

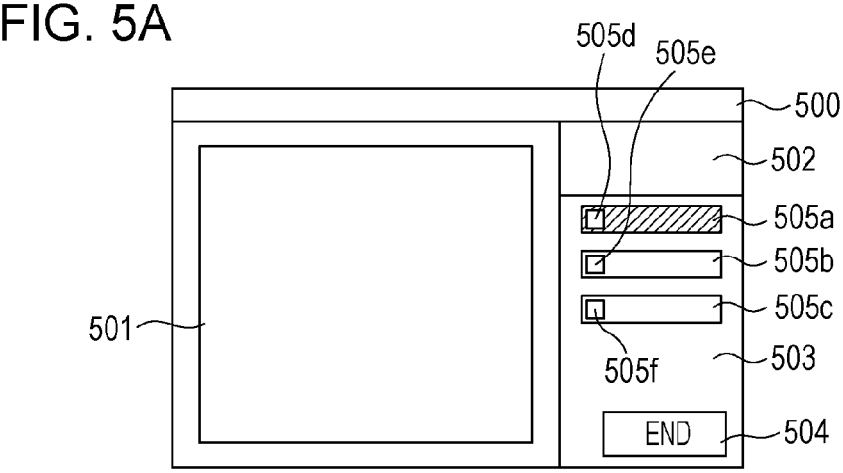
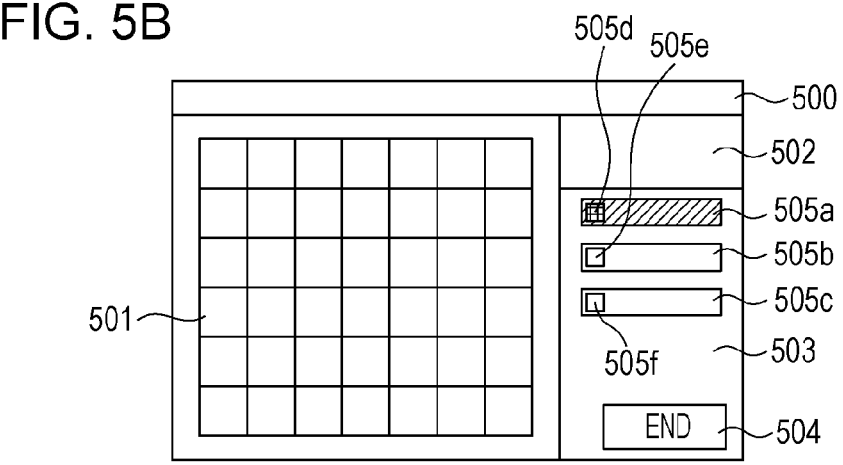
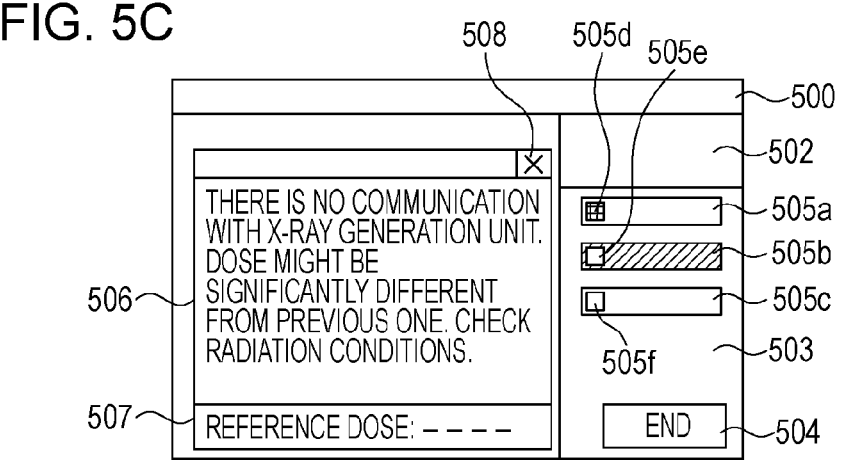

IMAGING MANAGEMENT APPARATUS, X-RAY IMAGING SYSTEM, METHOD FOR PROCESSING INFORMATION, AND PROGRAM

BACKGROUND OF THE INVENTION

Field of the Invention

The present disclosure relates to an imaging management apparatus, an X-ray imaging system, a method for processing information, and a program.

Description of the Related Art

In X-ray imaging, an X-ray reception unit that receives X-rays and obtains an X-ray image, an X-ray generation unit that emits X-rays to a subject, and an imaging management apparatus that manages information regarding the X-ray imaging by, for example, obtaining the X-ray image from the X-ray reception unit are used.

Information regarding tube current, tube voltage, the duration of radiation, and the like which are radiation conditions under which the X-ray generation unit emits X-rays, is set in accordance with an imaging region of the subject or an examination purpose. There are often predetermined radiation conditions for each imaging region or examination purpose. In Japanese Patent Application Laid-Open No. 2006-340910, a reference dose of radiation is determined on the basis of subject information, and if an estimated dose of radiation exceeds the reference dose, a warning is displayed.

Radiation conditions might be manually set for the X-ray generation unit from an operation panel, and an error, lack of setting, and other mistakes can occur in such a manual operation. If a plurality of X-ray imaging operations are sequentially performed using the X-ray generation unit and doses of radiation to be used are significantly different from one another because of different imaging regions between the X-ray imaging operations, for example, an X-ray imaging operation might be performed with an inappropriate dose due to an error in setting.

SUMMARY OF THE INVENTION

The present invention provides an imaging management apparatus that obtains an X-ray image as a result of X-ray imaging performed by an X-ray reception unit and an X-ray generation unit and that manages information regarding the X-ray imaging. The imaging management apparatus includes a first obtaining unit configured to obtain information regarding a dose in a first X-ray imaging operation performed by the X-ray generation unit and the X-ray reception unit, a second obtaining unit configured to obtain, after X-ray radiation corresponding to the first X-ray imaging operation but before X-ray radiation corresponding to a second X-ray imaging operation, which is managed by the imaging management apparatus and performed after the first X-ray imaging operation, information regarding a dose in the second X-ray imaging operation, and an output control unit configured to cause, after the X-ray radiation corresponding to the first X-ray imaging operation but before the X-ray radiation corresponding to the second X-ray imaging operation, an output unit to issue a warning on the basis of a difference between a value based on the information regarding the dose in the first X-ray imaging operation and a value based on the information regarding the dose in the second X-ray imaging operation.

Further features of the present invention will become apparent from the following description of exemplary embodiments with reference to the attached drawings.

BRIEF DESCRIPTION OF THE DRAWINGS

FIG. 4 is a flowchart illustrating information processing for managing information relating X-ray imaging performed by an X-ray reception unit and an X-ray generation unit according to an embodiment.

FIGS. 5A to 5C are diagrams illustrating examples of a display screen displayed on a display unit.

DESCRIPTION OF THE EMBODIMENTS

Figure 1:
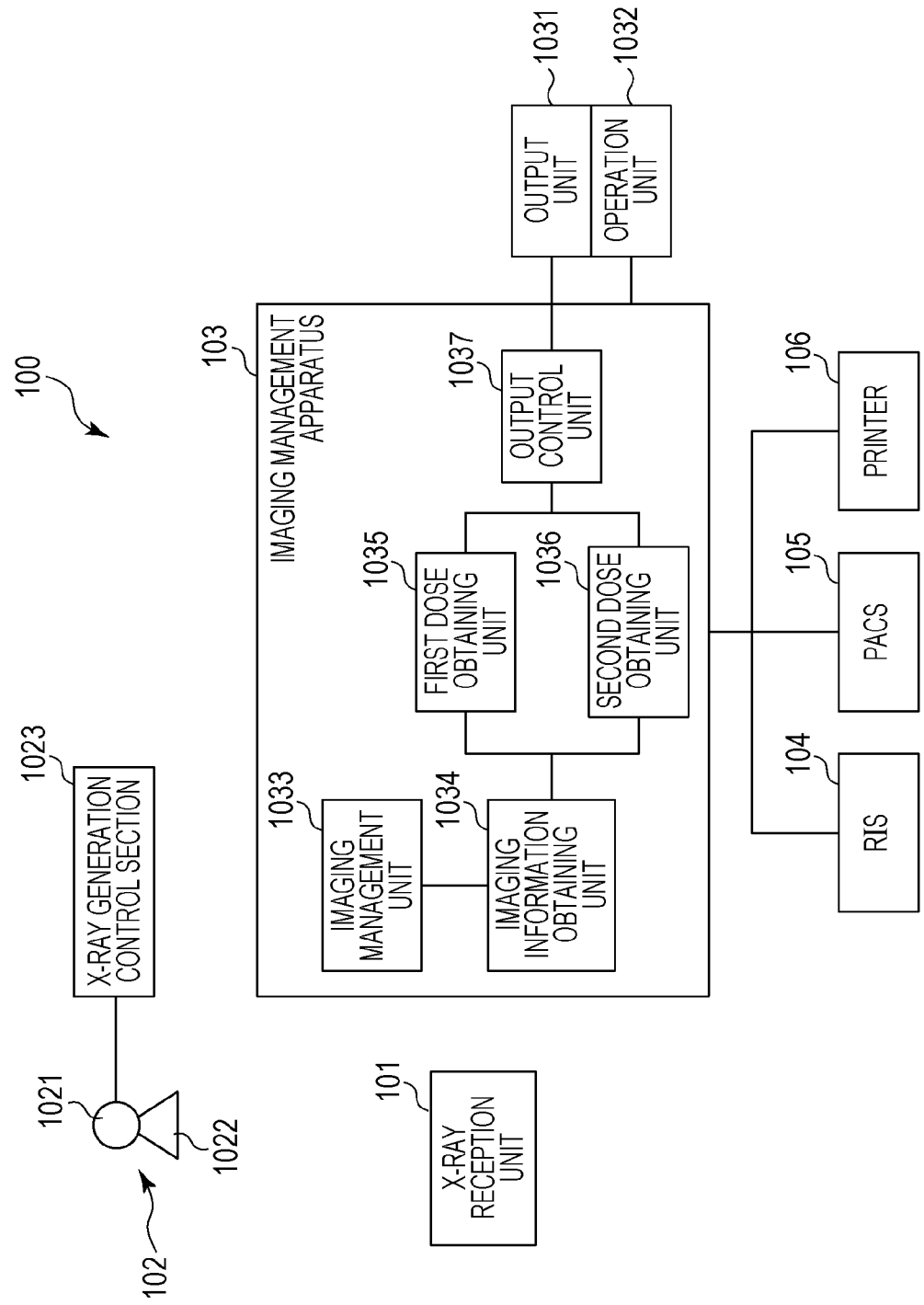
FIG. 1 is a block diagram illustrating the configuration of an X-ray imaging system according to an embodiment.
Figure 2:
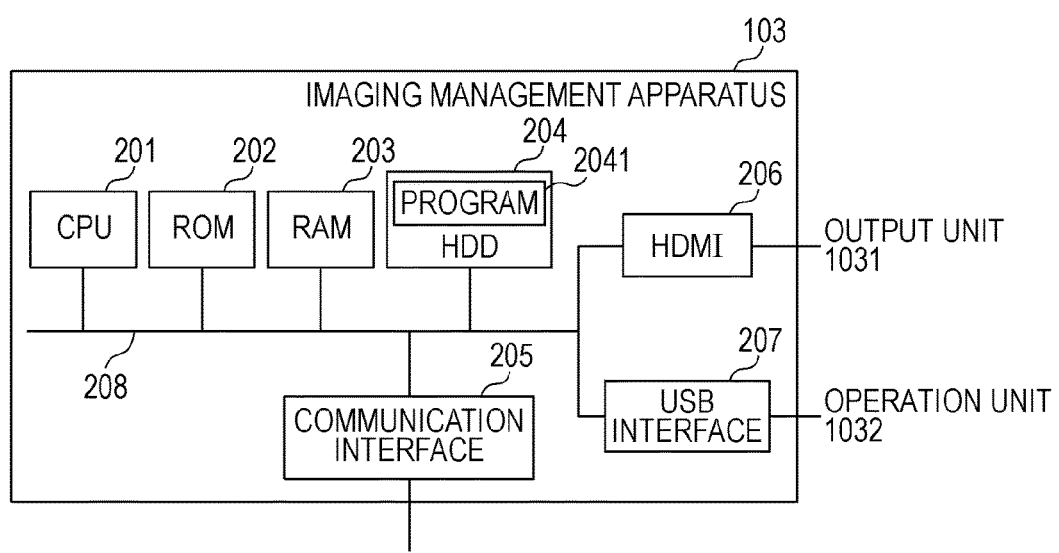
FIG. 2 is a diagram illustrating the hardware configuration of an imaging management apparatus.

An X-ray imaging system according to an embodiment of the present invention will be described with reference to FIG. 1. The X-ray imaging system includes an X-ray reception unit 101 that obtains an X-ray image, an X-ray generation unit 102, and an imaging management apparatus 103. The X-ray reception unit 101 is, for example, a film cassette that includes an X-ray film, a CR cassette that includes an imaging plate used for CR, or a digital X-ray sensor (DR sensor) that includes an X-ray detection array including photoelectric conversion elements arranged in two dimensions. The X-ray generation unit 102 includes an X-ray source 1021 including a target that receives high-speed electron beams to generate X-rays, a diaphragm 1022 that shapes the generated X-rays, and an X-ray generation control section 1023 that controls the X-ray source 1021.

An output unit 1031 that outputs information is connected to the imaging management apparatus 103. The imaging management apparatus 103 obtains an X-ray image obtained as a result of X-ray imaging performed by the X-ray reception unit 101 and the X-ray generation unit 102 and manages information regarding the X-ray imaging. The imaging management apparatus 103 includes an imaging information obtaining unit 1034, a first dose obtaining unit 1035, a second dose obtaining unit 1036, and an output control unit 1037. The imaging information obtaining unit 1034 obtains a plurality of pieces of imaging information corresponding to a plurality of X-ray imaging operations from an external apparatus or an internal memory. The first dose obtaining unit 1035 obtains information regarding a dose in a first X-ray imaging operation among the plurality of X-ray imaging operations. The second dose obtaining unit 1036 obtains information regarding an estimated dose for a second X-ray imaging, which is performed after the first X-ray imaging operation. As used herein, when referring to the X-ray imaging operations, the terms "first" and "second" are merely used to distinguish a temporal difference between two sequential X-ray imaging operations occurring one after the other. Therefore, the terms "first" and "second" do not limit the X-ray imaging operations to only two, as the concept of issuing a warning can be applied to any number of sequential X-ray imaging operations. The information regarding an estimated dose is obtained in order for the output control unit 1037 to cause the output unit 1031 to issue a warning based on the information regarding an estimated dose as necessary before the second (or subsequent) X-ray imaging operation is performed.

The output control unit 1037 obtains a difference between the dose in the first X-ray imaging operation and the estimated dose in the second X-ray imaging operation and causes the output unit 1031 to issue a warning on the basis of the difference. With this configuration, a warning can be issued in accordance with the difference. A user can be warned of a change in the dose between imaging operations, and inappropriate radiation due to lack of setting of the radiation conditions can be suppressed. If a difference between a value based on information regarding the dose in the first imaging operation and the estimated dose for the second imaging operation is larger than a threshold, for example, the output control unit 1037 causes the output unit 1031 to issue a warning based on the difference. If the difference is large, an inappropriate imaging operation is likely to occur, and the warning is issued to warn the user against inappropriately performing the second X-ray imaging operation. In another embodiment, if the estimated dose in the second X-ray imaging operation is higher than the dose in the first X-ray imaging operation, the output unit 1031 issues a warning indicating that an image might be obtained with insufficient radiation due to lack of setting of the radiation conditions. If the estimated dose in the second X-ray imaging operation is lower than the dose in the first X-ray imaging operation, the output unit 1031 issues a warning indicating that inappropriate radiation might occur due to lack of setting of the radiation conditions. Since the output control unit 1037 controls the issuance of a warning using information regarding the difference between the dose in the first X-ray imaging operation and the estimated dose for the second X-ray imaging operation, an appropriate warning can be issued in accordance with a situation. In this manner, erroneous or unnecessary imaging due to inappropriate radiation dosage can be prevented.

If the value based on the information regarding the dose in the first X-ray imaging operation and the estimated dose for the second X-ray imaging operation is smaller than the threshold, the output control unit 1037 inhibits the output unit 1031 from issuing a warning based on the difference. In doing so, an unnecessary warning is not issued, thereby realizing appropriate issuance of warnings.

The first dose obtaining unit 1035 may use an estimated dose or an actual dose measured by a dosimeter or the like as the information regarding the dose in the first X-ray imaging operation. The first dose obtaining unit 1035 obtains, for example, at least information regarding a standard dose associated with an imaging region in the first X-ray imaging operation, information regarding a dose associated with imaging information regarding the first X-ray imaging operation, or information regarding a dose calculated from an X-ray image obtained as a result of the first X-ray imaging operation. Alternatively, the first dose obtaining unit 1035 obtains at least information regarding radiation conditions under which X-rays have been radiated from the X-ray generation unit 102 in the first X-ray imaging operation or information regarding a dose obtained by measuring a dose of X-rays emitted from the X-ray generation unit 102 in the first X-ray imaging operation. In an embodiment, the imaging management apparatus 103 is connected to a dosimeter whose detection unit, such as a photomultiplier, is provided between an X-ray emission port or the diaphragm 1022 of the X-ray generation unit 102 and the X-ray reception unit 101, and the first dose obtaining unit 1035 receives information regarding a dose from the dosimeter.

The second dose obtaining unit 1036 obtains information regarding a dose obtained on the basis of information regarding standard radiation conditions associated with imaging information regarding the second X-ray imaging operation as the information regarding the estimated dose in the second X-ray imaging operation. The standard radiation conditions may be, for example, an average, a median, and a mode of each parameter included in radiation conditions used when, in the past, a plurality of X-ray images were obtained by capturing images of the same imaging region as in the second X-ray imaging operation. Alternatively, information regarding doses used when, in the past, a plurality of X-ray images were obtained by capturing images of the same imaging region as in the second X-ray imaging operation may be used as the information regarding the estimated dose in the second X-ray imaging operation.

If the X-ray reception unit 101 is a digital X-ray sensor, the imaging management apparatus 103 may include a wired or wireless communication circuit that communicates with the X-ray reception unit 101 and that receives an X-ray image obtained by the digital X-ray sensor. Alternatively, the imaging management apparatus 103 may include a communication circuit that communicates with the X-ray generation unit 102.

An operation unit 1032 that receives an operation performed by the user may be connected to the imaging management apparatus 103. In this case, the order of imaging operations can be set by, for example, sequentially specifying a plurality of pieces of imaging information obtained by the imaging information obtaining unit 1034. An imaging management unit 1033 manages the order of imaging operations and associates X-ray images obtained as a result of imaging operations and the pieces of imaging information with each other. The imaging management unit 1033 associates the X-ray images and the pieces of imaging information with each other by, for example, giving common IDs to the pieces of imaging information and the X-ray images as additional information.

A radiology information system (RIS) 104 that provides a plurality of pieces of imaging information for the imaging management apparatus 103 may be connected to the imaging management apparatus 103. In this case, the imaging information obtaining unit 1034 includes a communication circuit that receives the imaging information from the RIS 104. If a picture archiving and communication system (PACS) 105 is connected to the imaging management apparatus 103, the imaging management apparatus 103 transmits an X-ray image obtained as a result of X-ray imaging through a communication circuit thereof. If a printer 106 is connected to the imaging management apparatus 103, the imaging management apparatus 103 transmits an X-ray image obtained as a result of X-ray imaging through the communication circuit thereof in order to print the X-ray image.

The hardware configuration of the imaging management apparatus 103 will be described. The imaging management apparatus 103 is realized, for example, through a combination of a computer and a program including commands to be read and executed by the computer. The imaging management apparatus 103 includes, for example, a central processing unit (CPU) 201, a read-only memory (ROM) 202, a random-access memory (RAM) 203, a hard disk drive (HDD) 204, a communication interface 205, a high-definition multimedia interface (HDMI; registered trademark) 206, and a universal serial bus (USB) interface 207, or a plurality of each of these components, that are connected to one another by a bus 209. The HDD 204 is used for storing a program 2041 including commands for realizing functions and processes according to the present embodiment. The program 2041 is loaded into the RAM 203. The CPU 201 executes the commands included in the program stored in the RAM 203 or the ROM 202 to realize the functions and the processes according to the present embodiment. The communication interface 205 is a communication circuit used for communication when the imaging management apparatus 103 is connected to the RIS 104, the PACS 105, or the printer 106. The HDMI 206 is an interface with or a connection port for the output unit 1031. The USB interface 207 is an interface with or a connection port for the operation unit 1032.

Figure 3:
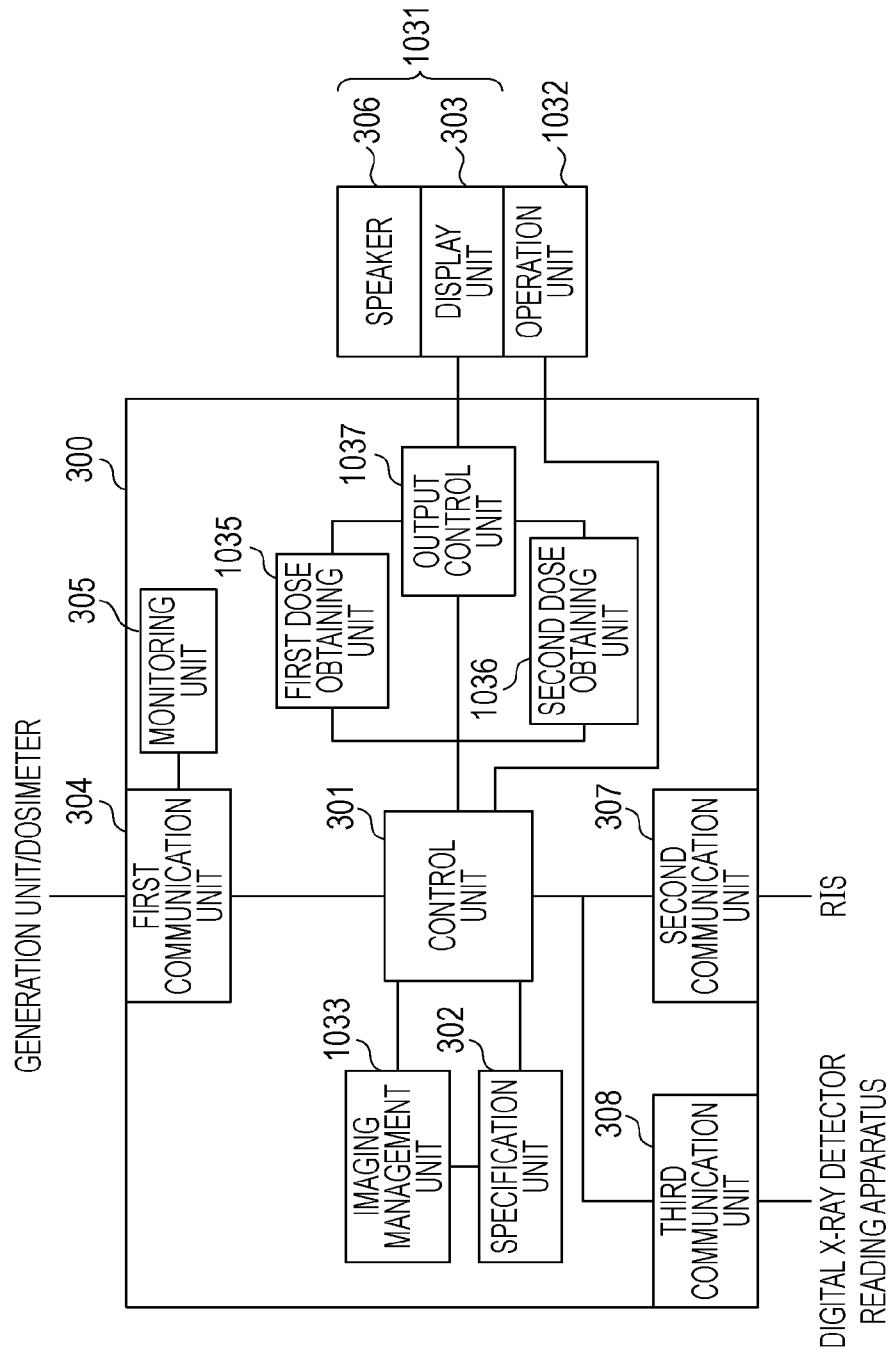
FIG. 3 is a diagram illustrating functions of an imaging management apparatus according to another embodiment.

An imaging management apparatus 300 according to another embodiment will be described with reference to FIG. 3. The imaging management apparatus 300 is obtained by adding a control unit 301 that integrally controls the imaging management apparatus 300 and other various components that will be described hereinafter to the imaging management apparatus 103 according to the above embodiment.

The imaging management apparatus 300 according to the present embodiment includes a specification unit 302 that specifies imaging information. The imaging management apparatus 300 might be connected to the X-ray generation unit 102.

After the first X-ray imaging operation is performed, the specification unit 302 specifies imaging information corresponding to the second X-ray imaging operation, which is different from the first X-ray imaging operation, as imaging information regarding an X-ray imaging operation performed after the first X-ray imaging operation. Imaging information is sequentially specified on the basis of, for example, the order of imaging operations stored in a memory, information regarding the order of a plurality of pieces of imaging information, or information regarding identifiers (IDs).

It is assumed, for example, that the operation unit 1032 and a display unit 303, which is the output unit 1031, are connected to the imaging management apparatus 300 and the output control unit 1037 displays a plurality of pieces of imaging operation on the display unit 303. In this case, after an operation for selecting one of the plurality of pieces of imaging information displayed on the display unit 303 is performed, the specification unit 302 specifies the selected piece of imaging information as imaging information regarding a next X-ray imaging operation. After the X-ray generation unit 102 emits X-rays to start the next X-ray imaging operation with the imaging information specified, the imaging management unit 1033 associates an X-ray image obtained as a result of the X-ray imaging operation and the specified imaging information with each other.

If imaging information is specified after the first X-ray imaging operation is performed as described above, the next X-ray imaging operation is automatically specified. If imaging information is specified in accordance with an operation performed using the operation unit 1032, the user can arbitrarily set the order of imaging operations.

After imaging information is specified, the control unit 301 causes a first communication unit 304 to transmit information regarding radiation conditions corresponding to the imaging information to the X-ray generation unit 102. If the imaging management apparatus 300 is connected to the X-ray generation unit 102, therefore, the information regarding radiation conditions is transmitted to the X-ray generation unit 102 through the first communication unit 304.

The imaging information includes, for example, information indicating an imaging region such as a chest, an abdomen, or a head, information indicating an imaging direction such as backward or forward, and information indicating an imaging method such as still image capture, fluoroscopy, or long moving image capture. The imaging information may also include information regarding standard radiation conditions corresponding to the imaging region, the imaging direction, and the imaging method. The information regarding radiation conditions includes information regarding tube current, tube voltage, the duration of radiation, and the like. The imaging information may also include information indicating a type of X-ray reception unit used for imaging. The information indicating the type of X-ray reception unit used for imaging may include information regarding the size of a DR sensor or the like as well as information regarding the type of X-ray reception unit such as a film cassette, CR cassette, or a DR sensor. The imaging information may also include information regarding an imaging position such as a standing position, a reclining position, or a free position.

If the information regarding radiation conditions is associated with the imaging information such as when the imaging information includes the information regarding radiation conditions, the control unit 301 obtains, after the specification unit 302 specifies the imaging information, corresponding information regarding radiation conditions and supplies the information regarding radiation conditions to the first communication unit 304.

The control unit 301 also determines whether the first communication unit 304 can transmit (has transmitted) the radiation conditions. If the X-ray generation unit 102 and the first communication unit 304 are not physically connected to each other, for example, the control unit 301 determines that the first communication unit 304 cannot transmit the radiation conditions. If the connection is established, the control unit 301 determines that the first communication unit 304 can transmit the radiation conditions. If the connection is established but the first communication unit 304 has not received a radiation condition reception notification (ACK) from the X-ray generation unit 102, the control unit 301 determines that the first communication unit 304 has failed to transmit the radiation conditions. If the first communication unit 304 has received the ACK, the control unit 301 determines that the first communication unit 304 has transmitted the radiation conditions.

If the control unit 301 cannot cause the first communication unit 304 to transmit the information regarding radiation conditions, the output control unit 1037 causes the output unit 1031 to issue a warning. On the other hand, if the first communication unit 304 can transmit the radiation conditions, the transmitted radiation conditions are set in the X-ray generation unit 102 to update the X-ray generation unit 102 for the second X-ray imaging operation. In this case, since the warning might not be necessary, the output control unit 1037 inhibits the output unit 1031 from issuing a warning. This can be realized by not supplying, to the output unit 1031, a signal for issuing a warning.

The imaging management apparatus 300 according to the present embodiment includes a monitoring unit 305 that monitors communication between the X-ray generation unit 102 and the imaging management apparatus 300. The monitoring unit 305 monitors a communication state on the basis of the state of the first communication unit 304 and information communicated between the X-ray generation unit 102 and the imaging management apparatus 300. If there is an abnormality in the communication, the monitoring unit 305 outputs a signal indicating that there has been an abnormality to the control unit 301. As described above, it can be determined whether there has been an abnormality in the communication in accordance with presence or absence of an ACK.

If the output control unit 1037 receives, from the control unit 301, a signal indicating that there has been an abnormality, that is, if there is an abnormality in the communication, the output control unit 1037 causes the output unit 1031 to issue a warning based on the dose difference. If there is no abnormality, the output control unit 1037 inhibits the output unit 1031 from issuing a warning based on the dose difference. By providing the monitoring unit 305 that monitors the communication state, too, a warning can be issued to the user as necessary.

In another embodiment, an information obtaining unit that obtains function information regarding the X-ray generation unit 102 may be provided. In this case, the output control unit 1037 controls the issuance of a warning on the basis of the function information. If the X-ray generation unit 102 has a function of issuing a warning according to the present embodiment, for example, the warning is not necessary. A warning can thus be issued in accordance with the function of the X-ray generation unit 102.

The function information according to an embodiment is, for example, information indicating that the X-ray generation unit 102 is an X-ray generation unit that maintains the setting of X-ray radiation conditions until the setting is manually changed or information indicating that the X-ray generation unit 102 is an X-ray generation unit that initializes the setting of X-ray radiation conditions before each X-ray radiation operation. If the function information is the former information, for example, the radiation conditions need to be set for each imaging operation, and it is advantageous to issue a warning according to this embodiment. If the function information is the latter information, a warning based on a difference from a dose in a previous imaging operation is not necessary. From this perspective, if the X-ray generation unit 102 is an X-ray generation unit that maintains the setting of X-ray radiation conditions until the setting is manually changed, the output control unit 1037 causes the output unit 1031 to issue a warning. If the X-ray generation unit 102 is an X-ray generation unit that initializes the setting of X-ray radiation conditions before each X-ray radiation operation, the output control unit 1037 inhibits the output unit 1031 from issuing a warning. In doing so, a warning can be issued at an appropriate timing while preventing an unnecessary warning.

The information obtaining unit that obtains the function information according to an embodiment reads the function information from a memory on the basis of, for example, an ID of the X-ray generation unit 102 connected to the imaging management apparatus 300. In this case, the control unit 301, for example, functions as the information obtaining unit. In another embodiment, the information obtaining unit receives the function information from the X-ray generation unit 102 connected thereto. In this case, the first communication unit 304 functions as the first communication unit 304.

In doing so, if there is no communication with the X-ray generation unit 102 or if the imaging management apparatus 103 does not have a function of setting radiation conditions for the X-ray generation unit 102, it is possible to reduce the possibility of an inappropriate dose due to lack of setting of the radiation conditions for the X-ray generation unit 102.

The imaging management apparatus 300 may be connected to the display unit 303 or a speaker 306, which is an audio output unit, as the output unit 1031. The output unit 1031 may be implemented by a visual output unit such as an LCD screen, an audio output unit such as a speaker, a haptic output unit such as a vibrating device for the tactile sense. If the display unit 303 is connected, the output control unit 1037 performs display control, in which information indicating the above-described warning based on the dose difference is displayed on the display unit 303. If the speaker 306 is connected, the output control unit 1037 causes the speaker 306 to output a voice indicating the warning. In these cases, the output control unit 1037 includes, for example, the HDMI 206. The output control unit 1037 may perform both types of control. Alternatively, a touch panel display in which the output control unit 1037 and the operation unit 1032 are integrated with each other may be used.

The imaging management apparatus 300 may also include a second communication unit 307 different from the first communication unit 304. The first communication unit 304 includes, for example, a USB interface, and the second communication unit 307 includes an Ethernet® interface. In an embodiment, the second communication unit 307 is connected to the RIS 104, the PACS 105, the printer 106, or a network inside or outside a hospital connected to the RIS 104, the PACS 105, and the printer 106. The second communication unit 307 corresponds to the communication interface 205. The second communication unit 307 functions as a reception unit that receives imaging information regarding a plurality of X-ray imaging operations.

The imaging management apparatus 300 may also include a third communication unit 308 different from the first communication unit 304 and the second communication unit 307. If the X-ray reception unit 101 is a digital X-ray sensor, the third communication unit 308 communicates with the X-ray reception unit 101 and receives an X-ray image obtained by the X-ray reception unit 101. If the X-ray reception unit 101 is a CR cassette, the third communication unit 308 communicates with a reader that reads a latent image obtained by the X-ray reception unit 101 and receives an X-ray image obtained by the reader. The first, second, and third communication units 304, 307, and 308 may be directly connected to the X-ray generation unit 102, the RIS 104, and the X-ray reception unit 101, or may communicate with the X-ray generation unit 102, the RIS 104, and the X-ray reception unit 101 through a relay such as an access point. The first, second, and third communication units 304, 307, and 308 may be communication units capable of performing wireless communication. Alternatively, the imaging management apparatus 300 may be connected to a relay by a wire, and the relay and a communication destination may wirelessly communicate with each other.

Information processing for managing imaging according to the present embodiment will be described with reference to a flowchart of FIG. 4. In step S401, the imaging information obtaining unit 1034 loads a plurality of pieces of imaging information corresponding to a plurality of X-ray imaging operations. In this processing, the imaging information obtaining unit 1034 may read the plurality of pieces of imaging information from the memory of the imaging management apparatus 103, or may receive the plurality of pieces of imaging information from the RIS 104.

In step S402, the X-ray generation unit 102 and the X-ray reception unit 101 perform the first X-ray imaging operation. The first X-ray imaging operation is an X-ray imaging operation corresponding to one of the plurality of pieces of imaging information obtained by the imaging information obtaining unit 1034. In step S403, the first dose obtaining unit 1035 obtains information regarding a dose in the first X-ray imaging operation. If the first dose obtaining unit 1035 uses radiation conditions used in the first X-ray imaging operation or a dose measured by the dosimeter or the like, step S402 and step S403 are performed in this order. If the first dose obtaining unit 1035 obtains an estimated dose in the first X-ray imaging operation in another embodiment, step S402 and step S403 may be switched.

In step S404, the second dose obtaining unit 1036 obtains information regarding an estimated dose in the second X-ray imaging operation, which is an X-ray imaging operation corresponding to one of the plurality of pieces of imaging information obtained by the imaging information obtaining unit 1034 and performed after the first X-ray imaging operation. As the estimated dose, a dose used for obtaining a past image of the same imaging region as in the second X-ray imaging operation or a dose set as a standard value for the imaging region is used.

In step S405, the output control unit 1037 calculates a difference d between the information regarding the dose in the first X-ray imaging operation and the estimated dose in the second X-ray imaging operation. In step S406, the output control unit 1037 determines whether the difference d exceeds a threshold. If the difference d exceeds the threshold, the process proceeds to step S407, and a warning indicating that X-ray imaging might be performed under inappropriate radiation conditions is issued. As described above, the warning is issued as a voice or information on a display.

In step S408, the X-ray generation unit 102 and the X-ray reception unit 101 perform the second X-ray imaging operation. The second X-ray imaging operation is an X-ray imaging operation corresponding to one of the plurality of pieces of imaging information obtained by the imaging information obtaining unit 1034 different from the one corresponding to the first X-ray imaging operation.

By issuing a warning in step S407 after X-ray radiation corresponding to the first X-ray imaging operation (S402) but before X-ray radiation corresponding to the second X-ray imaging operation (S408), a warning can be issued to the user in order to appropriately perform the second X-ray imaging operation, thereby reducing the possibility of an inappropriate imaging operation.

Figure 6:
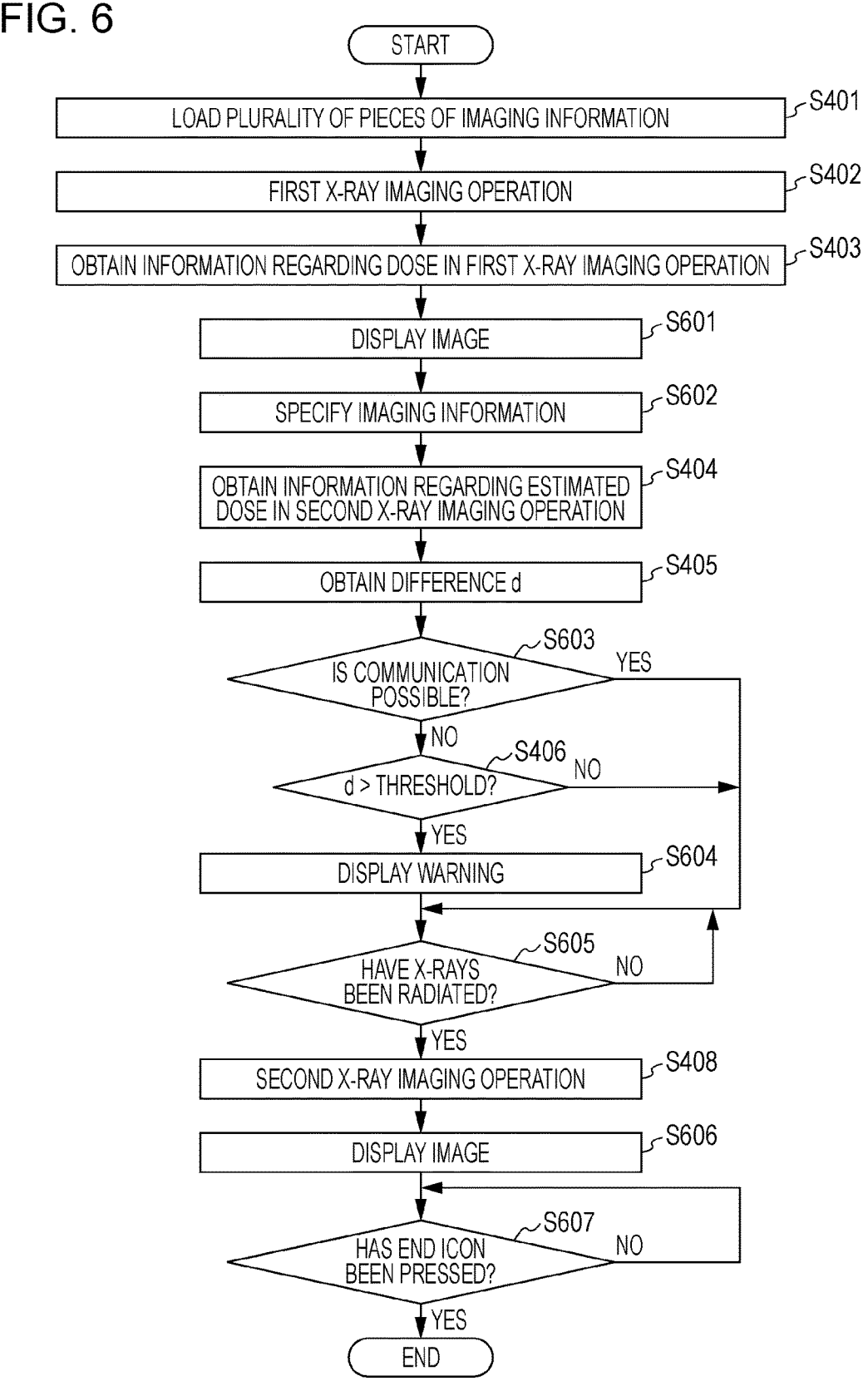
FIG. 6 is a flowchart illustrating information processing according to another embodiment.

A display screen 500 displayed by the output control unit 1037 on the display unit 303 when the display unit 303 and the operation unit 1032 are connected to the imaging management apparatus 300 will be described with reference to FIGS. 5A to 5C. A process illustrated in a flowchart of FIG. 6 will also be described in accordance with changes in the display screen 500. FIG. 5A illustrates the display screen 500 after a plurality of pieces of imaging information are obtained in step S401. FIG. 5B illustrates the display screen 500 after the first X-ray imaging operation is performed in step S402. FIG. 5C illustrates the display screen 500 after a warning is displayed in step S407. Steps illustrated in the flowchart of FIG. 6 having the same reference numerals as those illustrated in FIG. 4 are the same steps as those illustrated in FIG. 4, and description thereof is omitted.

The display screen 500 includes an image area 501 for displaying a captured X-ray image, a subject area 502 for displaying information regarding a subject, an imaging information area 503 for displaying imaging information, and an end icon 504 for ending an examination. In the imaging information area 503, a plurality of pieces of imaging information is displayed. In an embodiment, as illustrated in FIG. 5A, a first information area 505a corresponding to first imaging information corresponding to the first X-ray imaging operation, a second information area 505b corresponding to second imaging information corresponding to the second X-ray imaging operation, and a third information area 505c corresponding to third imaging information corresponding to a third X-ray imaging operation are displayed. In an embodiment, a first thumbnail area 505d, a second thumbnail area 505e, and a third thumbnail area 505f in which thumbnails of X-ray images obtained in the first to third imaging operations corresponding to the first to third imaging information are arranged in the first, second, and third information areas 505a, 505b, and 505c, respectively. A message or an icon indicating information included in the imaging information, such as imaging positions, imaging directions, and imaging methods, may be displayed in the first to third information areas 505a to 505c.

In FIG. 5A, the imaging information obtaining unit 1034 has obtained a plurality of pieces of imaging information (S401), and the specification unit 302 has specified the first imaging information. The output control unit 1037 controls display modes of the first to third information areas 505a to 505c such that specified information and information that has not been specified are distinguished from each other.

If the X-ray reception unit 101 is a digital X-ray sensor and the X-ray reception unit 101 and the imaging management apparatus 300 can communicate with each other through the third communication unit 308, the following process is performed. That is, after the imaging information is specified, the control unit 301 generates a control signal for supplying power to the X-ray detection array included in the X-ray reception unit 101 and transmits the control signal through the third communication unit 308. The X-ray reception unit 101 thus begins to prepare to receive X-rays.

The X-ray generation unit 102 generates X-rays (S402), and the X-ray reception unit 101 obtains an X-ray image. The imaging management apparatus 300 receives the X-ray image, and the output control unit 1037 displays the image on the display unit 303 (S601). FIG. 5B illustrates this state. The first dose obtaining unit 1035 has obtained information regarding a dose in the first X-ray imaging operation (S403).

In FIG. 5B, the X-ray image is displayed in the image area 501, and a thumbnail of the X-ray image is displayed in the first thumbnail area 505d corresponding to the first imaging information. An image processing unit configured by the CPU 201 of the imaging management apparatus 300 may perform a noise reduction process, tone conversion, a sharpening process, and the like on the X-ray image, and the X-ray image subjected to the image processing may be displayed. If the imaging management apparatus 300 includes a graphic processing unit (GPU), the GPU may perform the image processing. If a server for performing image processing is connected to the imaging management apparatus 300 through the second communication unit 307, the server for performing image processing may perform the image processing.

After the first X-ray imaging operation ends, the specification unit 302 specifies the second imaging information corresponding to the second X-ray imaging operation as illustrated in FIG. 5C (S602). In accordance with the specification, the output control unit 1037 automatically displays the second information area 505b in a display mode by which the second information area 505b can be distinguished from the other information areas 505a and 505c. If the specification unit 302 specifies imaging information in accordance with an operation performed using the operation unit 1032, the output control unit 1037 displays, in accordance with the specification, an information area corresponding to the specified imaging information in a display mode by which the information area can be distinguished from the other information areas.

In accordance with the specification performed by the specification unit 302, the second dose obtaining unit 1036 obtains information regarding an estimated dose in the second X-ray imaging operation, which is an X-ray imaging operation corresponding to one of the plurality of pieces of imaging information obtained by the imaging information obtaining unit 1034 and performed after the first X-ray imaging operation (S404). The output control unit 1037 calculates the difference d between the dose in the first X-ray imaging operation and the estimated dose in the second X-ray imaging operation (S405).

In step S603, the control unit 301 or the monitoring unit 305 determines whether communication with the X-ray generation unit 102 is possible or whether radiation conditions have been transmitted. If it is determined that there is an abnormality in the communication, the output control unit 1037 determines whether the difference d exceeds the threshold (S406). If the output control unit 1037 determines that the difference d exceeds the threshold, the output control unit 1037 displays a warning 506 on the display unit 303 in step S604 as illustrated in FIG. 5C.

In the present embodiment, if it is determined that communication cannot be performed or has failed, a process for displaying a warning (S406 and S604) is performed because it is likely that the radiation conditions are not automatically set and have not been set. It is therefore possible to suppress an inappropriate X-ray imaging operation. Alternatively, if the process for determining the communication state performed in step S603 is performed before step S403 and, if it is determined that communication cannot be performed or has failed, the process for displaying a warning performed in steps S403, S406, and S604 is performed, and an unnecessary process can be reduced, which is advantageous.

In doing so, if there is no communication with the X-ray generation unit 102 or if the imaging management apparatus 103 does not have a function of setting radiation conditions for the X-ray generation unit 102, it is possible to reduce the possibility of an inappropriate dose due to lack of setting of the radiation conditions for the X-ray generation unit 102.

The warning 506 according to an embodiment illustrated in FIG. 5C includes a message or an icon indicating that X-ray radiation might be performed with a dose significantly different from that in the previous imaging operation. The warning 506 corresponds to a warning based on a dose difference between imaging operations. A message or an icon indicating that there is no communication with the X-ray generation unit 102 or that communication has failed may also be displayed. A message or an icon asking the user to check the radiation conditions may also be displayed.

The output control unit 1037 may also display the estimated dose in the second X-ray imaging operation as a dose 507. In doing so, the user is given an opportunity to set X-ray radiation conditions on the basis of the estimated dose in the second X-ray imaging operation, which can reduce the possibility of an error in setting.

After the specification is performed in step S602, the processing in steps S404, S405, S603, and S406 is sequentially performed, and the output control unit 1037 displays the warning 506 in step S604 in accordance with the specified imaging information. The warning 506 can thus be issued to the user before the second X-ray imaging operation.

The warning 506 and the dose 507 may be displayed, for example, in the same window and can be hidden by pressing an icon 508 for hiding the window. A trigger for hiding the warning 506 is not limited to this, and the warning 506 may be automatically hidden after being displayed for a certain period of time.

If a digital X-ray sensor is used as the X-ray reception unit 101, the control unit 301 does not transmit the control signal for supplying power to the X-ray detection array while the warning 506 is displayed. After the warning 506 is hidden, the control unit 301 transmits the control signal. By performing control such that X-ray imaging becomes possible only after the user checks the warning 506, the user can check the warning 506 more certainly.

If it is determined that the difference d does not exceed the threshold or that there is no abnormality in the communication, a warning is not necessary. The process proceeds to step S605 without issuing a warning.

In step S605, radiation performed by the X-ray generation unit 102 is waited for, and if the X-ray generation unit 102 emits X-rays (YES in step S605), the X-ray reception unit 101 performs the second X-ray imaging operation in step S408. In step S606, the output control unit 1037 displays an X-ray image obtained as a result of the second X-ray imaging operation in the image area 501 of the display screen 500 of the display unit 303 instead of the X-ray image obtained as a result of the first X-ray imaging operation.

In step S607, an operation for pressing the end icon 504 is waited for, and if the end icon 504 is pressed, the process ends.

By issuing a warning in this manner to the user, inappropriate radiation due to lack of setting of the radiation conditions can be suppressed.

X-ray imaging systems according to other embodiments will be described with reference to FIGS. 7A to 12B.

In FIGS. 7A to 12B, an imaging control apparatus 703 and an examination information recognition apparatus 707 correspond to the imaging management apparatus 103 (300), a DR sensor 704 and a CR cassette 708 correspond to the X-ray reception unit 101 according to an embodiment, a generation device communication unit 811 corresponds to the first communication unit 304, an RIS communication unit 813 and a PACS communication unit 814 correspond to the second communication unit 307, a sensor communication unit 815 corresponds to the third communication unit 308, a region standard dose saving unit 819 corresponds to part of the first dose obtaining unit 1035, an imaging dose estimation and measurement unit 820 and an imaging dose estimation unit 1139 correspond to the second dose obtaining unit 1036, and an imaging dose checking and warning unit 816, an image display unit 817, and a warning display unit 1136 correspond to the output unit 1031. A control unit 812 corresponds to the control unit 301, a modality worklist (MWL) saving unit 818 corresponds to the imaging information obtaining unit 1034, a previous imaging information saving unit 821 corresponds to the imaging management unit 1033, and a region information comparison unit 822 and an imaging dose comparison unit 823 correspond to the output control unit 1037.

Figure 7C:
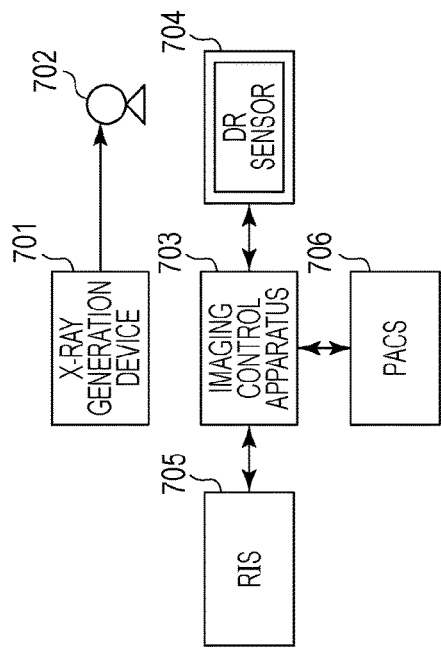
FIGS. 7A to 7D are diagrams illustrating configurations of X-ray imaging systems adopting a digital radiography (DR) method or a computed radiography (CR) method.
Figure 7D:
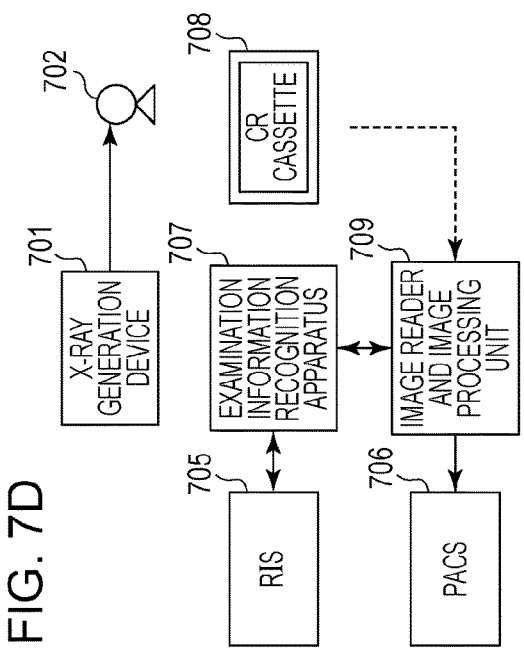
Figure 7A:
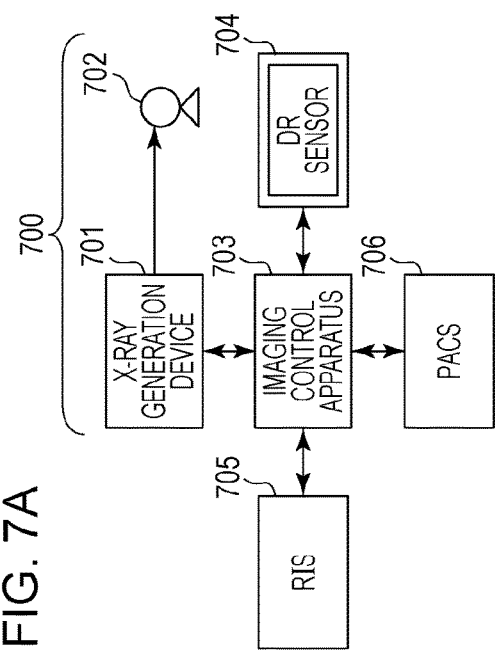

FIG. 7A illustrates the configuration of an X-ray imaging system adopting a DR method. The X-ray imaging system according to this embodiment includes an X-ray generation apparatus 700 including an X-ray generation device 701, an X-ray radiation unit 702 that emits X-rays when controlled by the X-ray generation device 701, and the imaging control apparatus 703 that captures an X-ray image accumulated by the DR sensor 704, and the DR sensor 704 that transmits, to the imaging control apparatus 703, an X-ray image captured synchronously with the X-ray radiation performed by the X-ray radiation unit 702. A RIS 705 that communicates subject information and examination information with the imaging control apparatus 703 and a PACS 706 that receives and saves an X-ray image captured by the imaging control apparatus 703 are connected to the X-ray imaging system.

With the configuration illustrated in FIG. 7A, X-ray imaging is usually performed in the following procedure. First, the RIS 705 transmits subject information and imaging information, such as a region and an imaging dose, regarding X-ray imaging to be performed to the imaging control apparatus 703. Upon receiving the subject information and the imaging information from the RIS 705, the imaging control apparatus 703 prepares for an imaging operation corresponding to the received imaging information. If the imaging information includes an imaging dose condition, the imaging control apparatus 703 transmits the imaging dose condition to the X-ray generation device 701. Upon receiving the imaging dose condition from the imaging control apparatus 703, the X-ray generation device 701 sets itself in such a way as to be able to emit X-rays in accordance with the received imaging dose condition and stands by for radiation. A dose to be used in actual X-ray radiation can be changed later to an arbitrary value from a value set by an operation performed by the user in accordance with the imaging dose condition. The imaging control apparatus 703 transmits the imaging dose condition to the X-ray generation device 701 and initializes settings of the DR sensor 704 in accordance with a region condition under which the imaging operation is to be performed. When the X-ray generation device 701 and the DR sensor 704 are ready, the imaging control apparatus 703 permits the X-ray generation device 701 to emit X-rays. The X-ray generation device 701 waits until an X-ray generation trigger switch included therein is pressed and, after the X-ray generation trigger switch is pressed, applies a current and a voltage according to the imaging dose to the X-ray radiation unit 702 to emit X-rays. While X-rays are being radiated, the DR sensor 704 accumulates an image and transmits the accumulated image to the imaging control apparatus 703. Upon receiving the image from the DR sensor 704, the imaging control apparatus 703 performs digital image processing on the obtained image and transmits the processed image to the PACS 706 to save the image. The X-ray imaging in which the DR sensor 704 is used is performed in the above-described procedure.

Figure 7B:
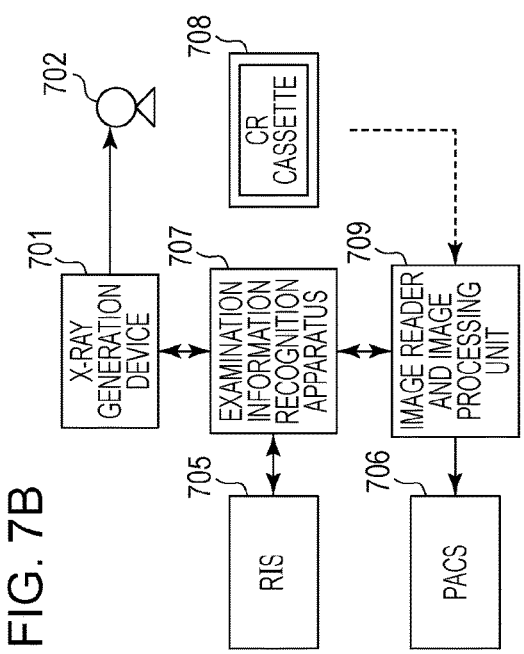

FIG. 7B illustrates the configuration of an X-ray imaging system adopting a CR method. In FIG. 7B, the components 701, 702, 705, and 706 are the same as those illustrated in FIG. 7A. In this embodiment, the CR cassette 708 is used instead of the DR sensor 704. In this embodiment, the X-ray imaging system includes the examination information recognition apparatus 707 that transmits subject information and imaging information received from the RIS 705 to the X-ray generation device 701 and an image reader and image processing unit 709, a CR cassette 708 that receives X-rays radiated from the X-ray radiation unit 702, that accumulates an X-ray image, and that digitizes the accumulated image using the image reader and image processing unit 709, and the image reader and image processing unit 709 that scans an image accumulated by the CR cassette 708, that digitizes the image, and that performs image processing on the image, and that transmits the image to the PACS 706.

With the configuration illustrated in FIG. 7B, X-ray imaging in which the CR cassette 708 is used is performed in the following procedure. First, the RIS 705 transmits subject information and imaging information, such as a region and an imaging dose, regarding X-ray imaging to be performed to the examination information recognition apparatus 707. Upon receiving the subject information and the imaging information from the RIS 705, the examination information recognition apparatus 707 prepares for an imaging operation corresponding to the received imaging information. If the imaging information includes an imaging dose condition, the examination information recognition apparatus 707 transmits the imaging dose condition to the X-ray generation device 701. Upon receiving the imaging dose condition from the examination information recognition apparatus 707, the X-ray generation device 701 sets itself in such a way as to be able to emit X-rays in accordance with the received imaging dose condition and stands by for radiation. A dose to be used in actual X-ray radiation can be changed later to an arbitrary value from a value set by an operation performed by the user in accordance with the imaging dose condition. The examination information recognition apparatus 707 might be integrated with the X-ray generation device 701. Because imaging conditions need not be set for the CR cassette 708 in advance, the user selects a CR cassette 708 that serves his/her purpose and sets the CR cassette 708 at an imaging position. When the X-ray generation device 701 and the CR cassette 708 are ready, the X-ray generation device 701 waits until the X-ray generation trigger switch included therein is pressed and, after the X-ray generation trigger switch is pressed, applies a current and a voltage according to the imaging dose to the X-ray radiation unit 702 to emit X-rays. While X-rays are being radiated, the CR cassette 708 accumulates an image. After the radiation of X-rays is completed, the user inserts the CR cassette 708 into the image reader and image processing unit 709. The image reader and image processing unit 709 scans the image accumulated by the CR cassette 708, digitizes the image, performs digital image processing on the image, and transmits the image to the PACS 706 to save the image. The X-ray imaging in which the CR cassette 708 is used is performed in the above-described procedure.

As described above, the X-ray generation device 701 reflects, using the imaging control apparatus 703 or the examination information recognition apparatus 707, an imaging dose included in imaging information regarding a certain subject transmitted from the RIS 705. As described above, automatically set X-ray radiation conditions can be changed to desired values through manual operations performed later by the user. Since default values of the X-ray radiation conditions are automatically set for each operation for capturing an image of a subject, incorrect X-ray radiation conditions cannot be used in imaging, unless the user intentionally or carelessly changes the default values.

FIGS. 7C and 7D illustrate configurations at a time when the X-ray generation device 701 is not connected to the imaging control apparatus 703 or the examination information recognition apparatus 707. The components illustrated in FIGS. 7C and 7D are the same as those illustrated in FIGS. 7A and 7B, respectively, but since the X-ray generation device 701 is not connected to the imaging control apparatus 703 or the examination information recognition apparatus 707, it is difficult for the imaging control apparatus 703 or the examination information recognition apparatus 707 to transmit imaging information (imaging dose information obtained from imaging region information and imaging conditions) received from the RIS 705 to the X-ray generation device 701 to set these pieces of information. In the cases illustrated in FIGS. 7C and 7D, therefore, the user needs to manually operate the X-ray generation device 701 to set an appropriate imaging dose for each imaging operation. It is also difficult for the imaging control apparatus 703 or the examination information recognition apparatus 707 to obtain a dose set for the X-ray generation device 701.

In the present embodiment, a possible inappropriate X-ray radiation condition set for the X-ray generation device 701 for a next imaging operation is detected and the user is warned of the inappropriate setting even if, as in FIGS. 7C and 7D, the X-ray generation device 701 is not connected to the imaging control apparatus 703 or the examination information recognition apparatus 707 or even in the case of an abnormality, that is, for example, a case in which the connection between the X-ray generation device 701 and the imaging control apparatus 703 or the examination information recognition apparatus 707 is broken for some reason although, as illustrated in FIGS. 7A and 7B, the X-ray generation device 701 is connected to the imaging control apparatus 703 or the examination information recognition apparatus 707.

Figure 8:
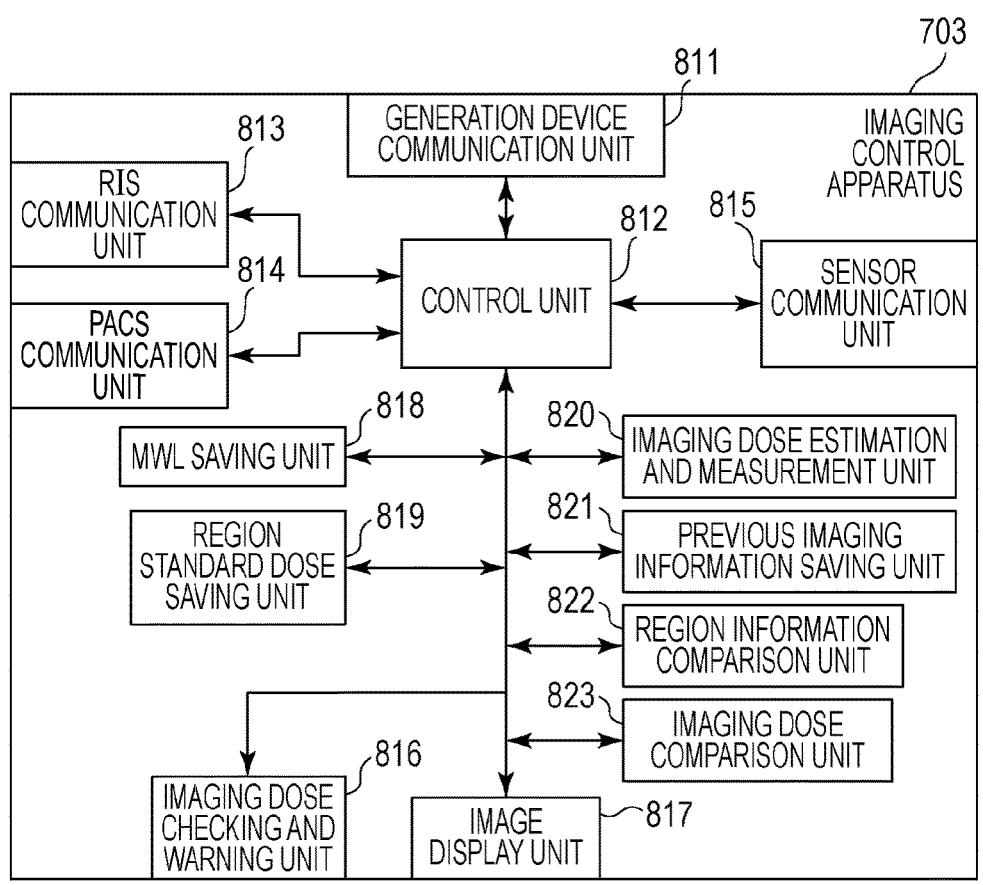
FIG. 8 is a diagram illustrating functions of an imaging control apparatus according to an embodiment.

FIG. 8 is a block diagram illustrating the imaging control apparatus 703 of a digital X-ray imaging system adopting the DR method in which the X-ray generation device 701 and the imaging control apparatus 703 do not communicate with each other as illustrated in FIG. 7C. In FIG. 8, a generation device communication unit 811 of the imaging control apparatus 703 communicates with the X-ray generation device 701. A control unit 812 controls the entirety of the imaging control apparatus 703. An RIS communication unit 813 communicates with the RIS 705. A PACS communication unit 814 communicates with the PACS 706. A sensor communication unit 815 communicates with the DR sensor 704. An imaging dose checking and warning unit 816 warns the user if a dose might be inappropriate for a current imaging operation. An image display unit 817 displays an X-ray image captured by the imaging control apparatus 703 and graphical user interfaces (GUIs). An MWL saving unit 818 saves imaging information (includes region information, X-ray information, and sensor conditions) obtained from the RIS 705 through the RIS communication unit 813. A region standard dose saving unit 819 saves a standard dose during an imaging operation for each imaging region. An imaging dose estimation and measurement unit 820 estimates a dose during an imaging operation from X-ray information and a captured image. A previous imaging information saving unit 821 saves imaging region information and the like in a previous imaging operation. A region information comparison unit 822 compares region information and the like in the previous imaging operation and region information and the like in a current imaging operation. An imaging dose comparison unit 823 compares a dose in the previous imaging operation and an estimated dose in the current imaging operation.

Figure 9:
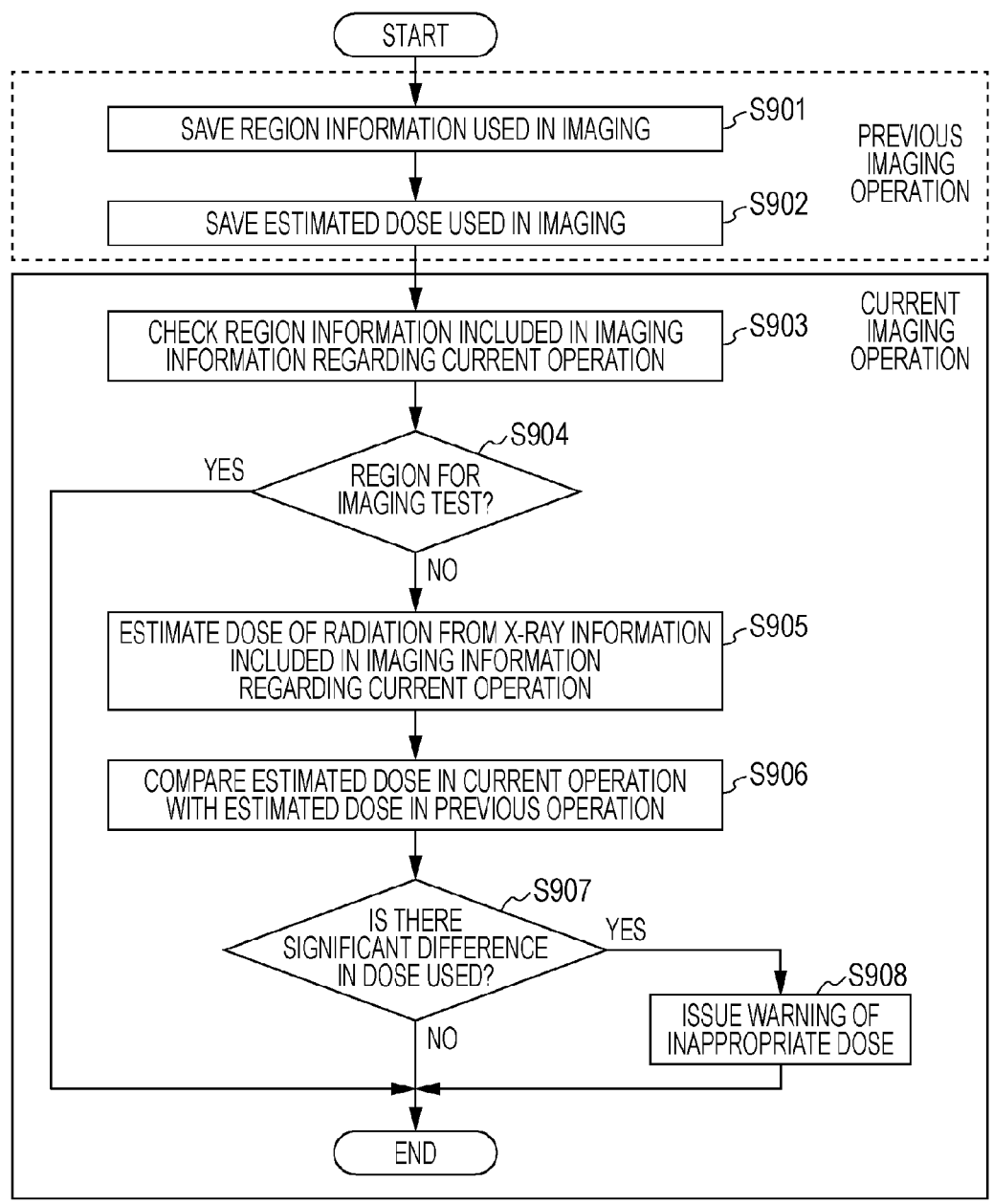
FIG. 9 is a flowchart illustrating a warning process performed by a system in which the imaging control apparatus is used.

FIG. 9 is a flowchart illustrating a process performed when the digital X-ray imaging system adopting the DR method warns the user of an inappropriate dose in a case in which the X-ray generation device 701 and the imaging control apparatus 703 do not communicate with each other as illustrated in FIG. 7C. First, in a first imaging operation, the imaging control apparatus 703 receives imaging information (includes region information, X-ray information, and sensor conditions) from the RIS 705 through the RIS communication unit 813 or obtains the imaging information through an operation manually performed by the user before the imaging operation starts. The control unit 812 analyzes the received imaging information and saves the region information, the X-ray information, the sensor conditions, and the like for the imaging operation to the MWL saving unit 818. At this time, the information saved to the MWL saving unit 818 may be only the region information or the X-ray information. If the X-ray generation device 701 and the imaging control apparatus 703 can communicate with each other, the X-ray information is transmitted to the X-ray generation device 701 through the generation device communication unit 811, and a dose is automatically set for the X-ray generation device 701. In this case, however, since the X-ray generation device 701 and the imaging control apparatus 703 do not communicate with each other, the automatic setting is not performed. Next, the control unit 812 transmits the received sensor conditions to the DR sensor 704 through the sensor communication unit 815 to prepare for the imaging operation. After the preparation is completed, the control unit 812 notifies the user of the completion through the image display unit 817. The user sets an optimal dose for the imaging operation by operating the X-ray generation device 701 and waits until the image display unit 817 indicates that the preparation has been completed. After confirming that the preparation has been completed, the user presses the X-ray generation trigger switch included in the X-ray generation device 701 to start the X-ray imaging. The DR sensor 704 detects X-rays and begins to accumulate an image. After completing the accumulation, the DR sensor 704 transmits the captured image to the imaging control apparatus 703. The sensor communication unit 815 of the imaging control apparatus 703 performs image processing on the image received from the DR sensor 704 and displays the image on the image display unit 817. The control unit 812 saves the region information used in the imaging operation to the previous imaging information saving unit 821 (S901) and calculates, using the imaging dose estimation and measurement unit 820, an estimated dose used in the imaging operation from the X-ray information saved in the MWL saving unit 818. The control unit 812 saves the estimated dose to the previous imaging information saving unit 821 (S902). The first imaging operation thus ends.

Another imaging operation then follows. At a beginning of this imaging operation, the dose set in the X-ray generation device 701 is estimated to be an optimal dose for the previous imaging operation. The optimal dose refers to a dose adjusted by the user on the basis of the X-ray information received from the RIS 705. The optimal dose is therefore not necessarily the same as the X-ray information received from the RIS 705, but there should be no significant difference between the optimal dose and the X-ray information.

In the current imaging operation, as in the previous imaging operation, the imaging control apparatus 703 receives imaging information (includes region information, X-ray information, and sensor conditions) from the RIS 705 through the RIS communication unit 813 or obtains the imaging information through an operation manually performed by the user before the imaging operation starts. The control unit 812 analyzes the received imaging information and saves the region information, the X-ray information, the sensor conditions, and the like for the imaging operation to the MWL saving unit 818. Next, the control unit 812 checks the region information used in the current imaging operation using the region information comparison unit 822 (5903) and, if the current imaging operation is an imaging operation performed for a test region (YES in S904), such as calibration or a quality check (QC), ends the process without warning the user of an inappropriate dose. On the other hand, if the region information for the current imaging operation does not indicate a test region (NO in S904), the control unit 812 transmits the X-ray information saved in the MWL saving unit 818 to the imaging dose estimation and measurement unit 820 to estimate a dose used in the current imaging operation (S905). The control unit 812 reads the estimated dose in the previous imaging operation saved to the previous imaging information saving unit 821 in the previous imaging operation and compares the estimated dose in the previous imaging operation with the estimated dose in the current imaging operation obtained by the imaging dose estimation and measurement unit 820 using the imaging dose comparison unit 823 (S906). If there is a significant difference between the estimated doses (YES in S907), the control unit 812 displays, on the image display unit 817, a message asking the user to check the imaging dose and warns, using the imaging dose checking and warning unit 816, the user of an inappropriate imaging dose through a voice or light (S908). The control unit 812 then ends the process. Alternatively, the warning may be issued only through the message or only through the voice or the light. On the other hand, if there is no significant differences between the estimated doses (NO in S907), the control unit 812 ends the process without issuing a warning.

By repeating the above-described second process, an X-ray imaging system can be realized that can issue a warning if there can be a significant difference in the imaging dose between a previous imaging operation and a current imaging operation. If the current imaging operation is just a test, the X-ray imaging system does not issue a warning even if there is a significant difference in the imaging dose between the previous imaging operation and the current imaging operation.

It is determined in the present embodiment whether to issue a warning by making comparisons with the imaging information regarding the current imaging operation using the region information (S904) used in the previous imaging operation and the dose (S907) estimated from the X-ray information used in the previous imaging operation. Whether to issue a warning, however, may be determined by making both comparisons or by making either comparison.

Figure 10:
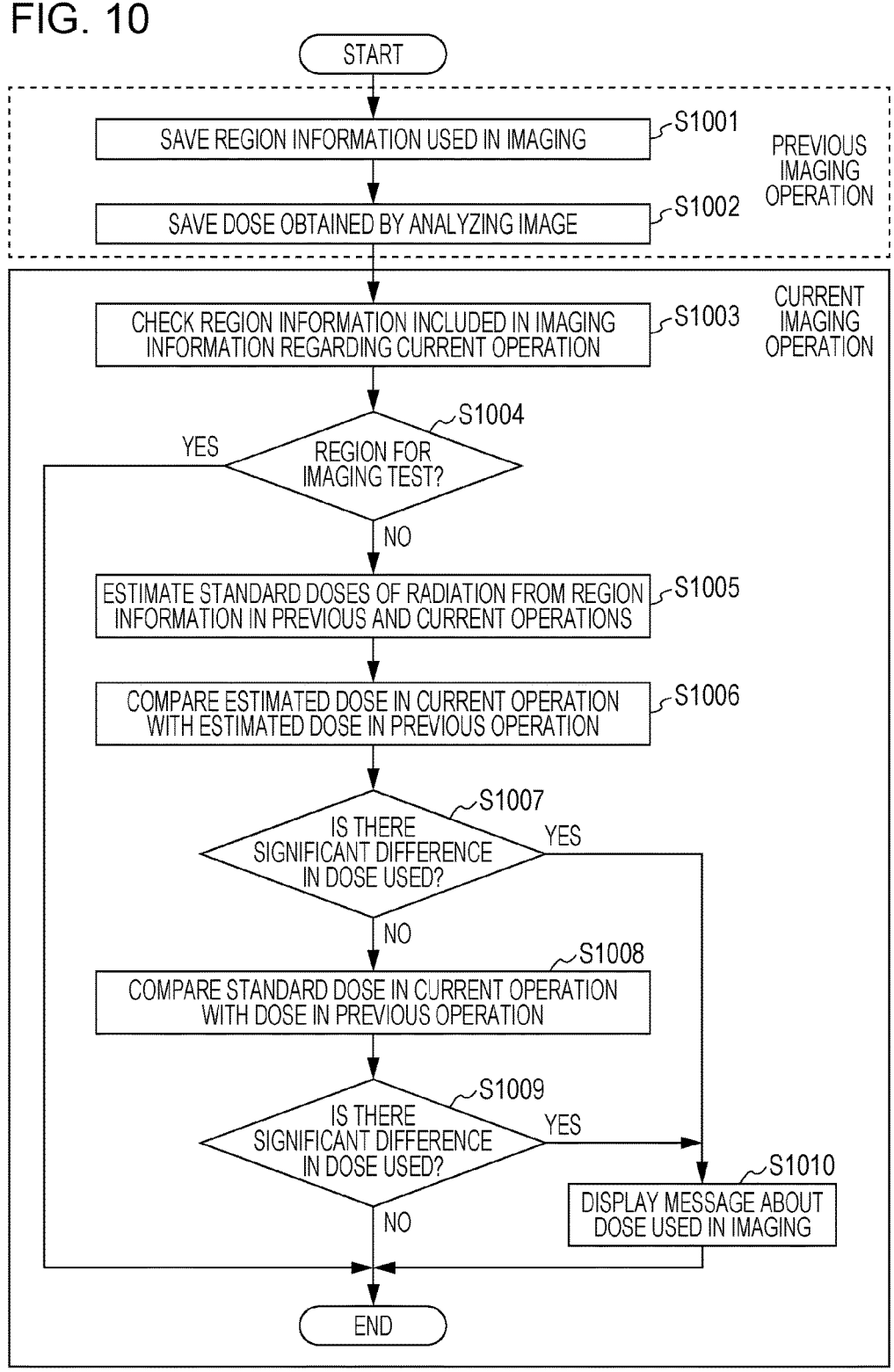
FIG. 10 is a flowchart illustrating a warning process performed by a system in which an examination information recognition apparatus is used.

In the above embodiment, a method for warning the user of an inappropriate dose used when, in a digital X-ray imaging system adopting the DR method in which the X-ray generation device 701 is not connected to the imaging control apparatus 703, X-ray information can be received from the RIS 705 as imaging information has been described. Depending on an operation mode, however, the imaging information received from the RIS 705 or obtained through an operation manually performed by the user might not include X-ray information. In a next embodiment, such a case will be described with reference to FIGS. 7C, 8, and 10. FIG. 10 is a flowchart illustrating a process performed when the digital X-ray imaging system adopting the DR method illustrated in FIG. 7C in which the X-ray generation device 701 and the imaging control apparatus 703 do not communicate with each other warns the user of an inappropriate dose under a condition in which it is difficult to receive X-ray information from the RIS 705 as imaging information.

In an operation realized by the present configuration, it is assumed that a common imaging dose for each imaging region is obtained and saved in the region standard dose saving unit 819 of the imaging control apparatus 703 in advance. First, in a first imaging operation, the imaging control apparatus 703 receives imaging information (includes region information and sensor conditions but does not include X-ray information) from the RIS 705 through the RIS communication unit 813 or obtains the imaging information through an operation manually performed by the user before the imaging operation starts. The control unit 812 analyzes the received imaging information and saves the region information, the sensor conditions, and the like for the imaging operation to the MWL saving unit 818. At this time, the information saved to the MWL saving unit 818 may be only the region information. Next, the control unit 812 transmits the received sensor conditions to the DR sensor 704 through the sensor communication unit 815 to prepare for the imaging operation. After the preparation is completed, the control unit 812 notifies the user of the completion through the image display unit 817. The user sets an optimal dose for the imaging operation by operating the X-ray generation device 701 and waits until the image display unit 817 indicates that the preparation has been completed. After confirming that the preparation has been completed, the user presses the X-ray generation trigger switch included in the X-ray generation device 701 to start the X-ray imaging. The DR sensor 704 detects X-rays and begins to accumulate an image. After completing the accumulation, the DR sensor 704 transmits the captured image to the imaging control apparatus 703. The sensor communication unit 815 of the imaging control apparatus 703 performs image processing on the image received from the DR sensor 704 and displays the image on the image display unit 817. The control unit 812 saves the region information used in the imaging operation to the previous imaging information saving unit 821 (S1001). The control unit 812 then analyzes, using the imaging dose estimation and measurement unit 820, the captured image and calculates a dose index such as an exposure index (EI). The control unit 812 saves the dose index to the previous imaging information saving unit 821 (S1002). The first imaging operation thus ends.

Another imaging operation then follows. At a beginning of this imaging operation, the dose set in the X-ray generation device 701 is estimated to be an optimal dose for the previous imaging operation. The optimal dose refers to a dose adjusted by the user on the basis of the region information received from the RIS 705. The imaging dose is adjusted in accordance with the imaging region or the state of the subject, and a reference dose for each region relating to the imaging region is saved in the region standard dose saving unit 819 in advance. The optimal dose is therefore not necessarily the same as the reference dose obtained from region information, but there should be no significant difference between the optimal dose and the reference dose.

In the current imaging operation, as in the previous imaging operation, the imaging control apparatus 703 receives imaging information (includes region information and sensor conditions) from the RIS 705 through the RIS communication unit 813 or obtains the imaging information through an operation manually performed by the user before the imaging operation starts. The control unit 812 analyzes the received imaging information and saves the region information, the sensor conditions, and the like for the imaging operation to the MWL saving unit 818. Next, the control unit 812 checks the region information used in the current imaging operation using the region information comparison unit 822 (S1003) and, if the current imaging operation is an imaging operation performed for a test region (YES in S1004), such as calibration or a QC, ends the process without warning the user of an inappropriate dose. On the other hand, if the region information for the current imaging operation does not indicate a test region (NO in S1004), the control unit 812 refers to the region standard dose saving unit 819 on the basis of the region information saved in the MWL saving unit 818 to obtain a standard dose corresponding to the region in the current imaging operation and refers to the region standard dose saving unit 819 on the basis of the imaging region information in the previous imaging operation saved in the previous imaging information saving unit 821 to obtain a standard dose corresponding to the region in the previous imaging operation (S1005). The control unit 812 compares the standard dose in the previous imaging operation with the standard dose in the current imaging operation using the imaging dose comparison unit 823 (S1006). If there is a significant difference between the estimated doses (YES in S1007), the control unit 812 displays, on the image display unit 817, a message asking the user to check the imaging dose and warns, using the imaging dose checking and warning unit 816, the user of an inappropriate imaging dose through a voice or light (S1010). The control unit 812 then ends the process. Alternatively, the warning may be issued only through the message or only through the voice or the light. On the other hand, if there is no significant differences between the estimated doses (NO in S1007), the control unit 812 reads the dose index such as an EI obtained as a result of the image analysis conducted in the previous imaging operation and saved in the previous imaging information saving unit 821. The control unit 812 then compares, using the imaging dose comparison unit 823, the dose index in the previous imaging operation with the standard dose in the current imaging operation (S1008). If there is a significant difference between the doses (YES in S1009), the control unit 812 displays, on the image display unit 817, a message asking the user to check the imaging dose and warns, using the imaging dose checking and warning unit 816, the user of an inappropriate imaging dose through a voice or light (S1010). The control unit 812 then ends the process. Alternatively, the warning may be issued only through the message or only through the voice or the light. On the other hand, if there is no significant differences between the estimated doses (NO in S1009), the control unit 812 ends the process without issuing a warning.

By repeating the above-described second process, an X-ray imaging system can be realized that can issue a warning if there can be a significant difference in the imaging dose between a previous imaging operation and a current imaging operation. If the current imaging operation is just a test, the X-ray imaging system does not issue a warning even if there is a significant difference in the imaging dose between the previous imaging operation and the current imaging operation.

It is determined in the present embodiment whether to issue a warning by making comparisons with the imaging information regarding the current imaging operation using the region information (S1004) used in the previous imaging operation, the standard dose (S1007) estimated from the imaging region information used in the previous imaging operation, and the dose index (S1009) obtained by analyzing the image captured in the previous imaging operation. Whether to issue a warning, however, may be determined by making all the three comparisons or by making one of the comparisons.

Figure 11:
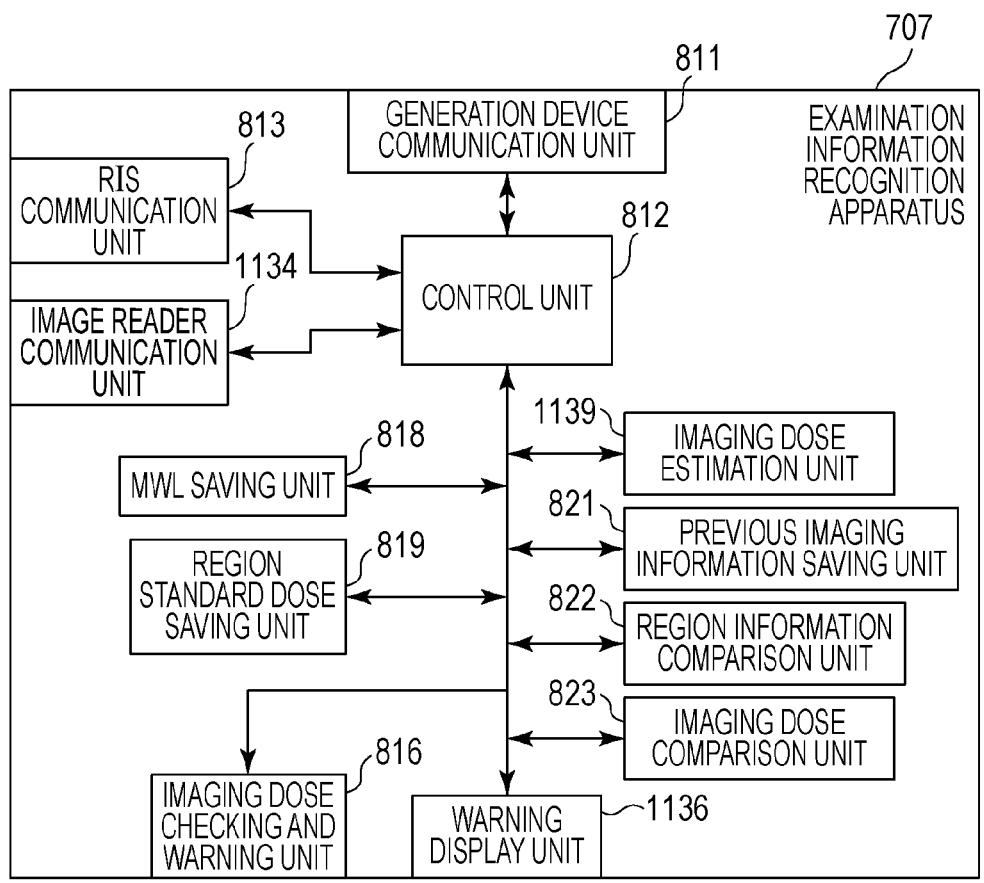
FIG. 11 is a diagram illustrating functions of the examination information recognition apparatus according to an embodiment.

In the above embodiment, a method for warning the user of an inappropriate dose used by a digital X-ray imaging system adopting the DR method in which there is no communication with the X-ray generation device 701 has been described. The same method may be used by a digital X-ray imaging system adopting the CR method in which there is no communication with the X-ray generation device 701. FIG. 11 is a block diagram illustrating the examination information recognition apparatus 707 in the digital X-ray imaging system adopting the CR method in which the X-ray generation device 701 and the examination information recognition apparatus 707 do not communicate with each other as illustrated in FIG. 7D. In FIG. 11, description of the same components as those illustrated in FIG. 8 is omitted. The examination information recognition apparatus 707 includes an image reader communication unit 1134 that performs communication for sharing RIS information with the image reader and image processing unit 709, a warning display unit 1136 that displays a warning if a dose might be inappropriate for a current imaging operation, and an imaging dose estimation unit 1139 that estimates a dose in an imaging operation from X-ray information.

The above-described method illustrated in FIG. 9 can be applied to the digital X-ray imaging system adopting the CR method in which there is no communication with the X-ray generation device 701 illustrated in FIGS. 7D and 11 just by omitting the processing relating to the communication with the DR sensor 704. The above-described method illustrated in FIG. 10, too, can be applied to the digital X-ray imaging system adopting the CR method in which there is no communication with the X-ray generation device 701 illustrated in FIGS. 7D and 11, but, in this case, the processing relating to the communication with the DR sensor 704 and the processing in steps S1002, S1008, and S1009 are omitted. The reason why the processing in steps S1002, S1008, and S1009 is omitted is that, in the CR method, it is difficult to obtain a dose from a captured image through an analysis unless the image reader and image processing unit 709 digitizes the captured image.

Figure 12A:
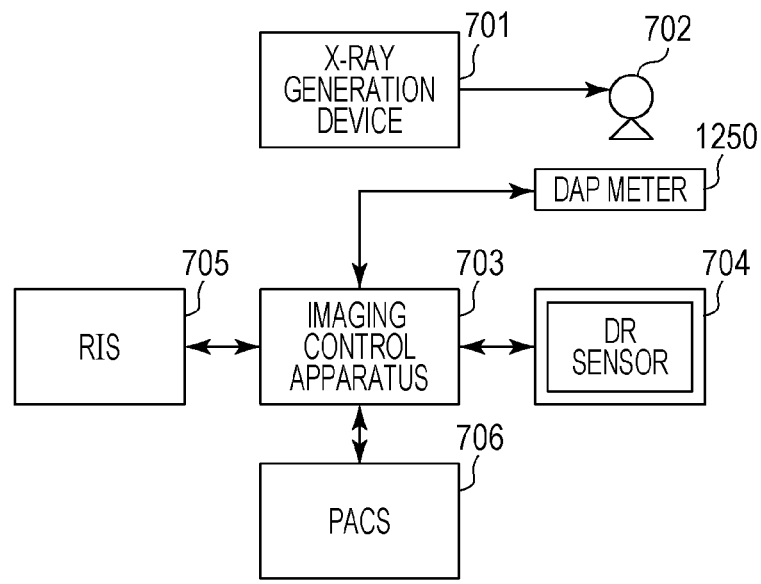
FIGS. 12A and 12B are diagrams illustrating configurations of X-ray imaging systems, in each of which a dose area product (DAP) meter is used.
Figure 12B:
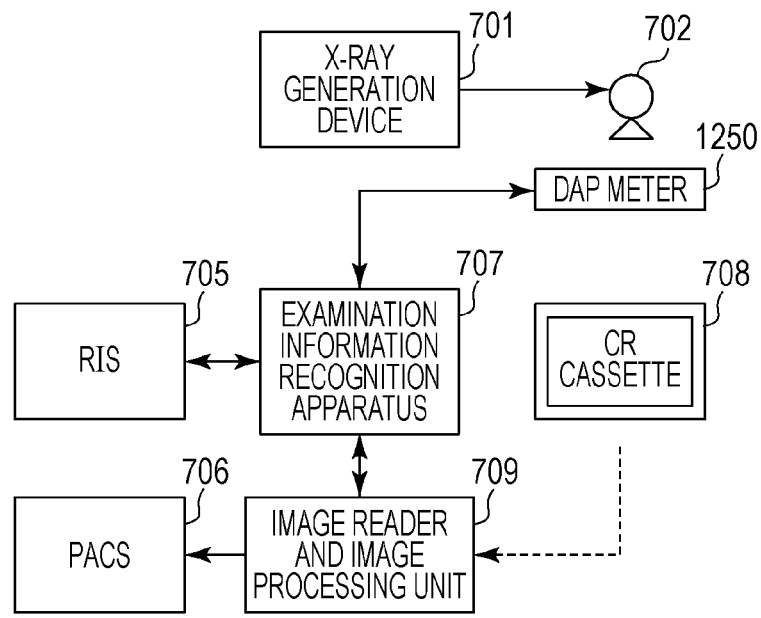

FIG. 12A illustrates the configuration of a digital X-ray imaging system adopting the DR method in which a DAP meter (dosimeter) 1250 is used. FIG. 12B illustrates the configuration of a digital X-ray imaging system adopting the CR method in which the DAP meter 1250 is used. The DAP meter 1250 is a device that measures a dose of generated X-rays. By connecting the DAP meter 1250 to the imaging control apparatus 703 or the examination information recognition apparatus 707, the imaging control apparatus 703 or the examination information recognition apparatus 707 can use an imaging dose measured by the DAP meter 1250. In the cases of FIGS. 12A and 12B, in which the DAP meter 1250 is connected, therefore, the same process as that illustrated in FIG. 10 can be performed by replacing a dose obtained in step S1002 by analyzing a captured image with a dose input from the DAP meter 1250, regardless of whether the digital X-ray imaging system adopts the DR method or the CR method. In this case, it is determined whether to issue a warning by making comparisons with imaging information regarding a current imaging operation using region information (S1004) regarding a previous imaging operation, a standard dose (S1007) estimated from imaging region information used in the previous imaging operation, and the dose input from the DAP meter 1250 in the previous imaging operation. Whether to issue a warning, however, may be determined by making all the three comparisons or by making one of the comparisons.

In the above embodiment, it is determined whether to issue a warning after a dose in a previous imaging operation is obtained from X-ray information, region information, a dose index measured from a captured image, or dose information obtained from the DAP meter 1250 and the dose in the previous image operation is compared with a dose estimated from X-ray information or region information in a current imaging operation received from the RIS 705. In the following case, however, a warning is not issued.

The above-described warning function is not necessary for a skilled user. A function of inhibiting the warning function by turning off the warning function is therefore provided, unless an unskilled user uses the warning function.

Because it is common to review the imaging conditions after a failed imaging operation, an excessive warning is not necessary even if there is a significant difference in the imaging dose between the failed previous imaging operation and a current imaging operation.

In the above embodiment, the imaging control apparatus 703 or the examination information recognition apparatus 707 saves previous imaging conditions. If a combination of the X-ray generation device 701 and the imaging control apparatus 703 or the examination information recognition apparatus 707 remains the same, a warning can be appropriately issued. If the combination changes, however, it is difficult to issue an appropriate warning in the above examples because region information, X-ray conditions, and a measured dose in a previous imaging operation saved in the system are no longer valid. Such a case can arise especially when two X-ray generation apparatuses are installed in a studio for the standing position and the reclining position but only one sensor is used. In this case, it can be determined whether to use the X-ray generation apparatus for the standing position or the X-ray generation apparatus for the reclining position on the basis of workspace information included in imaging information received from the RIS 705. It can therefore be determined between the previous imaging operation and the current imaging operation illustrated in FIGS. 9 and 10 whether workspace has changed. If the workspace has changed, a warning may be issued.

As described above, in an X-ray imaging system in which the X-ray generation device 701 is not connected to the imaging control apparatus 703 or the examination information recognition apparatus 707 or in an X-ray imaging system in which the X-ray generation device 701 is connected to the imaging control apparatus 703 or the examination information recognition apparatus 707 but there is no communication between these apparatuses for some reason, the X-ray generation device 701 or either the imaging control apparatus 703 or the examination information recognition apparatus 707 can store imaging information or an imaging dose in a previous imaging operation. After receiving imaging information in a current imaging operation from the RIS 705, the X-ray generation device 701 or either the imaging control apparatus 703 or the examination information recognition apparatus 707 can compare the imaging information or the imaging dose in the previous imaging operation with the imaging information and an estimated imaging dose in the current imaging operation to prepare for the current imaging operation. If it is determined that the dose used in the previous imaging operation and the dose used in the current imaging operation can be significantly different from each other, a warning is issued.

If it is estimated that the dose used in the previous imaging operation and the dose used in the current imaging operation are not significantly different from each other, or if it is estimated that no problem arises even through there is a significant difference between the doses, a warning is not issued.

By issuing a warning if current imaging conditions are significantly different from previous imaging conditions, the user is warned of the difference and can avoid, for example, capturing an image of a subject with an unexpectedly high dose.

In the X-ray generation unit 102, a single X-ray generation control section might be provided for a plurality of X-ray sources. In this case, there is virtually a plurality of X-ray generation units 102.

As another embodiment, an example will be described in which the technique described in the above embodiment is used for evaluating a dose of radiation used in a second X-ray imaging operation after the second X-ray imaging operation ends. In the present embodiment, unlike in the above embodiments, the output unit 1031 issues a warning after the second X-ray imaging operation. In the present embodiment, a determination unit that determines whether a dose used for obtaining an X-ray image has been appropriate is provided. Like the first dose obtaining unit 1035 or the like, the determination unit is realized by, for example, the CPU 201, the RAM 203, and the program 2041. The determination unit determines that the dose has been excessive if, for example, there are many pixels whose pixel values are equal to or larger than a certain value in a subject region of an X-ray image obtained as a result of an X-ray imaging operation. Alternatively, the determination unit determines whether the dose has been appropriate on the basis of a difference between standard dose information associated with imaging information regarding the X-ray imaging operation and actual dose information obtained by a dosimeter or the like. If the determination unit determines that the dose used for obtaining the X-ray image has been inappropriate, the output control unit 1037 causes the output unit 1031 to issue a warning indicating that the dose has been inappropriate. The user of the system can therefore easily identify a cause of an abnormality in the X-ray image and perform an appropriate imaging operation. This embodiment is effective when, for example, an appropriate dose or the standard dose information is not very reliable or when it is not desirable to issue a warning before an imaging operation.

Although the embodiments of the present invention have been described, the present invention is not limited to these embodiments and can be altered or modified in various ways without deviating from the scope thereof.

Figure 13:
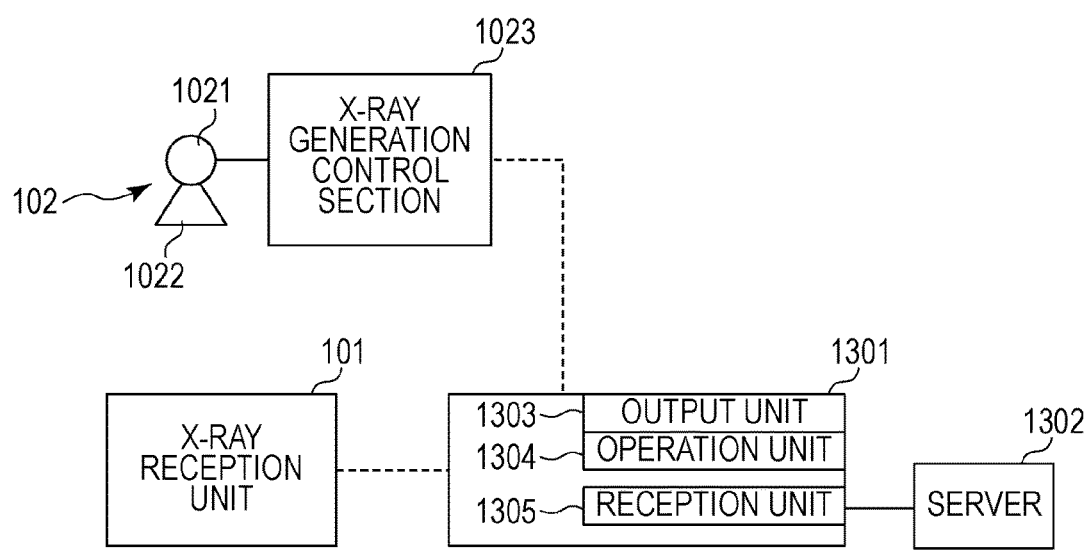
FIG. 13 is a diagram illustrating the configuration of an X-ray imaging system according to another embodiment.

In another embodiment of the present invention illustrated in FIG. 13, a plurality of devices performs the process originally performed by the imaging management apparatus 103. Components to which the same names and the same reference numerals as those mentioned above are given are the same as those according to the above embodiments, and description thereof is omitted.

In the present embodiment, the functions of the first dose obtaining unit 1035 and the second dose obtaining unit 1036 are provided outside an imaging management apparatus 1301 and realized by a server 1302 that communicates with a reception unit 1305 of the imaging management apparatus 1301. The functions may be realized, as in the above embodiments, by executing commands included in a program stored in the server 1302 using a CPU and a ROM of the server 1302. The reception unit 1305 receives information regarding a dose in a first X-ray imaging operation and an estimated dose in a second X-ray imaging operation calculated or obtained by the server 1302. In this sense, the reception unit 1305 functions as the first dose obtaining unit 1035 and the second dose obtaining unit 1036. Such a configuration is effective when the imaging management apparatus 1301 is a mobile terminal or the like whose throughput is low. In this case, the imaging management apparatus 1301 may be integrated with an output unit 1303 having the function of the output unit 1031 and an operation unit 1304 having the function of the operation unit 1032.

In an embodiment of the present invention, a software program (a program corresponding to one of the flowcharts in the drawings according to the above embodiments) for realizing the functions according to one of the above embodiments is directly or remotely supplied to a system or an apparatus, and a computer of the system or the apparatus reads and executes program codes of the supplied software program.

The program codes installed on the computer to realize the functions and the processes in the present invention are therefore also an embodiment of the present invention. The present invention also includes a World Wide Web (WWW) server that allows a plurality of users to download a program file for realizing the functions and the processes according to one of the embodiments of the present invention using computers. It is also possible to encode a program according to one of the embodiments of the present invention, distribute, to users, the program stored in a storage medium such as a compact disc read-only memory (CD-ROM), and allow users who satisfy a certain condition to download key information for decoding the program from a website on the Internet. The users can realize the functions and the processes according to one of the embodiments of the present invention by executing the program decoded using the key information and installing the program on the computers. In addition, the functions and the processes according to one of the above embodiments can be realized not only when a computer executes a read program but also when an operating system (OS) operating on the computer executes part or the entirety of actual processing on the basis of instructions from the program.

By issuing warnings in the above-described manners, the user can be warned of an inappropriate dose, and inappropriate radiation can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-206744, filed Oct. 7, 2014, which is hereby incorporated by reference herein in its entirety.

What is claimed is:

1. An imaging management apparatus that controls X-ray imaging to be performed at least two times on a subject by an X-ray reception unit and an X-ray generation unit and that manages information regarding the X-ray imaging, the imaging management apparatus comprising:
    a first obtaining unit configured to obtain information regarding a dose in a first X-ray imaging operation;
    a second obtaining unit configured to obtain, after X-ray radiation corresponding to the first X-ray imaging operation but before X-ray radiation corresponding to a second X-ray imaging operation, which is managed by the imaging management apparatus and subsequently performed after the first X-ray imaging operation, information regarding a dose in the second X-ray imaging operation; and
    an output control unit configured to cause, after the X-ray radiation corresponding to the first X-ray imaging operation but before the X-ray radiation corresponding to the second X-ray imaging operation, an output unit to issue a warning on the basis of a difference between a value based on the information regarding the dose in the first X-ray imaging operation and a value based on the information regarding the dose in the second X-ray imaging operation.

2. The imaging management apparatus according to claim 1, further comprising:
    a specification unit configured to specify imaging information regarding the X-ray imaging; and
    a control unit configured to transmit, after the imaging information is specified, information regarding an X-ray radiation condition corresponding to the imaging information to the X-ray generation unit,
    wherein the output control unit is configured to cause the output unit to issue the warning if the control unit is not able to transmit the information regarding an X-ray radiation condition.

3. The imaging management apparatus according to claim 1,
    wherein, if the X-ray generation unit and the imaging management apparatus are not connected to each other, the output control unit is configured to cause the output unit to issue the warning and, if the X-ray generation unit and the imaging management apparatus are connected to each other, inhibits the output unit from issuing the warning.

4. The imaging management apparatus according to claim 1, further comprising:
    a monitoring unit configured to monitor communication between the X-ray generation unit and the imaging management apparatus,
    wherein, if there is an abnormality in the communication, the output control unit causes the output unit to issue the warning and, if there is no abnormality in the communication, inhibits the output unit from issuing the warning.

5. The imaging management apparatus according to claim 1, further comprising:
    an information obtaining unit configured to obtain function information regarding the X-ray generation unit,
    wherein the output control unit controls the issuance of the warning on the basis of the function information.

6. The imaging management apparatus according to claim 1,
    wherein, if the X-ray generation unit maintains setting of the X-ray radiation condition until the setting is changed, the output control unit causes the output unit to issue the warning, and
    wherein, if the X-ray generation unit initializes the setting of the X-ray radiation condition before each X-ray radiation operation, the output control unit inhibits the output unit from issuing the warning.

7. The imaging management apparatus according to claim 1, further comprising:
    a detection unit configured to detect that the X-ray generation unit that communicates with the imaging management apparatus has changed, wherein, if the detection unit detects, after the X-ray radiation corresponding to the first X-ray imaging operation but before the X-ray radiation corresponding to the second X-ray imaging operation, that the X-ray generation unit has changed, the output control unit causes the output unit to issue the warning.

8. The imaging management apparatus according to claim 1,
wherein the output control unit displays information indicating the warning and the information regarding the dose in the second X-ray imaging operation obtained by the second obtaining unit on a display unit.

9. The imaging management apparatus according to claim 1, further comprising:
a display control unit configured to display first imaging information corresponding to the first X-ray imaging operation and second imaging information corresponding to the second X-ray imaging operation on a display unit; and
a specification unit configured to specify imaging information,
wherein, if the specification unit specifies the second imaging information, the output control unit causes the output unit to issue the warning.

10. The imaging management apparatus according to claim 1,
wherein, if the difference between the value based on the information regarding the dose in the first imaging operation and the value based on the information regarding the dose in the second imaging operation is larger than a threshold, the output control unit causes the output unit to issue the warning and, if the difference between the value based on the information regarding the dose in the first imaging operation and the value based on the information regarding the dose in the second imaging operation is smaller than a threshold, inhibits the output unit from issuing the warning.

11. The imaging management apparatus according to claim 1,
wherein the first obtaining unit obtains at least any of the following pieces of information as the information regarding the dose in the first X-ray imaging operation: information regarding a standard dose associated with an imaging region; information regarding a dose associated with imaging information regarding the first X-ray imaging operation; information regarding a dose calculated from an X-ray image obtained as a result of the first X-ray imaging operation; information regarding an X-ray radiation condition under which X-rays have been radiated from the X-ray generation unit in the first X-ray imaging operation; and information regarding a dose obtained by measuring a dose of X-rays radiated from the X-ray generation unit in the first X-ray imaging operation.

12. The imaging management apparatus according to claim 1,
wherein the first obtaining unit receives the information regarding the dose from a dosimeter whose detection unit is provided between an X-ray emission port of the X-ray generation unit and the X-ray reception unit.

13. The imaging management apparatus according to claim 1,
wherein the second obtaining unit obtains information regarding an estimated dose according to imaging information regarding the second X-ray imaging operation as the information regarding the dose in the second X-ray imaging operation.

14. The imaging management apparatus according to claim 12,
wherein the second obtaining unit obtains, as information regarding an estimated dose in the second X-ray imaging operation, information regarding a dose obtained on the basis of information regarding a standard radiation condition associated with imaging information regarding the second X-ray imaging operation.

15. The imaging management apparatus according to claim 1,
wherein the output control unit performs either display control, in which a display unit that is the output unit displays information indicating the warning, or control in which an audio output unit that is the output unit outputs a voice indicating the warning.

16. An X-ray imaging system comprising:
a reception unit configured to receive imaging information regarding X ray imaging to be performed at least two times on a subject by an X-ray generation unit and an X-ray reception unit;
a first obtaining unit configured to obtain information regarding a dose in a first X-ray imaging operation;
a second obtaining unit configured to obtain, after X-ray radiation corresponding to the first X-ray imaging operation but before X-ray radiation corresponding to a second X-ray imaging operation, which is managed by an imaging management apparatus and subsequently performed after the first X-ray imaging operation, information regarding a dose in the second X-ray imaging operation; and
an output control unit configured to cause, after the X-ray radiation corresponding to the first X-ray imaging operation but before the X-ray radiation corresponding to the second X-ray imaging operation, an output unit to issue a warning on the basis of a difference between a value based on the information regarding the dose in the first X-ray imaging operation and a value based on the information regarding the dose in the second X-ray imaging operation.

17. A method for processing information used for managing information regarding X-ray imaging to be performed at least two times on a subject by an X-ray reception unit and an X-ray generation unit, the method comprising the steps of: obtaining information regarding a dose in a first X-ray imaging operation;
obtaining, after X-ray radiation corresponding to the first X-ray imaging operation but before X-ray radiation corresponding to a second X-ray imaging operation, which is managed by an imaging management apparatus and subsequently performed after the first X-ray imaging operation, information regarding a dose in the second X-ray imaging operation; and
causing, after the X-ray radiation corresponding to the first X-ray imaging operation but before the X-ray radiation corresponding to the second X-ray imaging operation, an output unit to issue a warning on the basis of a difference between a value based on the information regarding the dose in the first X-ray imaging operation and a value based on the information regarding the dose in the second X-ray imaging operation.

* * * * *